(12) United States Patent
Shterzer

(10) Patent No.: US 12,257,449 B2
(45) Date of Patent: Mar. 25, 2025

(54) INTENSE PULSE LIGHT (IPL) APPARATUS UTILIZING A PULSE FORMING NETWORK (PFN)

(71) Applicant: Moshe Shterzer, Herzliya (IL)

(72) Inventor: Moshe Shterzer, Herzliya (IL)

( * ) Notice: Subject to any disclaimer, the term of this patent is extended or adjusted under 35 U.S.C. 154(b) by 648 days.

(21) Appl. No.: 16/984,375

(22) Filed: Aug. 4, 2020

(65) Prior Publication Data

US 2020/0360714 A1 Nov. 19, 2020

Related U.S. Application Data

(63) Continuation of application No. PCT/IL2019/050066, filed on Jan. 16, 2019.

(Continued)

(51) Int. Cl.
| | |
|---|---|
| *A61N 5/06* | (2006.01) |
| *H01J 61/02* | (2006.01) |
| *H01J 61/16* | (2006.01) |
| *H05B 41/34* | (2006.01) |
| *H05B 41/38* | (2006.01) |
| *A61B 18/18* | (2006.01) |

(52) U.S. Cl.
CPC .......... *A61N 5/0616* (2013.01); *H01J 61/025* (2013.01); *H01J 61/16* (2013.01); *H05B 41/34* (2013.01); *H05B 41/38* (2013.01); *A61B 18/18* (2013.01); *A61N 2005/0629* (2013.01); *A61N 2005/0654* (2013.01); *A61N 2005/0663* (2013.01); *A61N 2005/0666* (2013.01)

(58) Field of Classification Search
CPC .......... A61N 5/0616; A61N 2005/0629; A61B 18/18
See application file for complete search history.

(56) References Cited

U.S. PATENT DOCUMENTS

| 7,097,656 B1 | 8/2006 | Akopov et al. |
| 7,452,356 B2 | 11/2008 | Grove et al. |

(Continued)

FOREIGN PATENT DOCUMENTS

WO WO 2019/150359 8/2019

OTHER PUBLICATIONS

International Preliminary Report on Patentability Dated Aug. 20, 2020 From the International Bureau of WIPO Re. Application No. PCT/IL2019/050066. (6 Pages).

(Continued)

*Primary Examiner* — Lynsey C Eiseman
*Assistant Examiner* — Jessica L Mullins

(57) ABSTRACT

An IPL apparatus utilizing a Pulse Forming Network (PFN) for generating a plurality of light pulse sequences, comprising a treatment unit comprising one or more lamps adapted to emit a plurality of light pulses towards a treatment face of the IPL apparatus, a PFN and a control unit adapted to operate the PFN to generate a regulated energized pulse driven to the lamp(s). The regulated energized pulse having a desired multi-level voltage waveform with a maximum voltage level and a minimum voltage level which is in a range of 30-50 percent of the maximum voltage level. Rapidly varying heat is induced by a sequence of the plurality of light pulses emitted by the lamp(s) according to the multi-level voltage waveform.

20 Claims, 19 Drawing Sheets

(8 of 19 Drawing Sheet(s) Filed in Color)

Related U.S. Application Data

(60) Provisional application No. 62/626,200, filed on Feb. 5, 2018.

(56) References Cited

U.S. PATENT DOCUMENTS

| | | | |
|---|---|---|---|
| 2003/0069567 A1 | 4/2003 | Eckhouse et al. | |
| 2004/0030325 A1* | 2/2004 | Cahir | A61B 18/203 |
| | | | 606/9 |
| 2009/0306636 A1* | 12/2009 | Ben-Israel | H05K 7/20136 |
| | | | 606/9 |
| 2011/0125227 A1 | 5/2011 | Vaynberg et al. | |
| 2012/0010684 A1 | 1/2012 | Owens et al. | |
| 2012/0143288 A1 | 6/2012 | Owens et al. | |
| 2013/0345685 A1* | 12/2013 | Poran | A61B 18/20 |
| | | | 606/9 |
| 2014/0327426 A1 | 11/2014 | Shterzer | |
| 2015/0126980 A1* | 5/2015 | Levi | A61B 18/203 |
| | | | 606/9 |
| 2016/0263392 A1* | 9/2016 | Dietz | A61N 5/0616 |
| 2017/0246331 A1* | 8/2017 | Lloyd | A61Q 17/04 |

OTHER PUBLICATIONS

International Search Report and the Written Opinion Dated Apr. 17, 2019 From the International Searching Authority Re. Application No. PCT/IL2019/050066. (16 Pages).

* cited by examiner

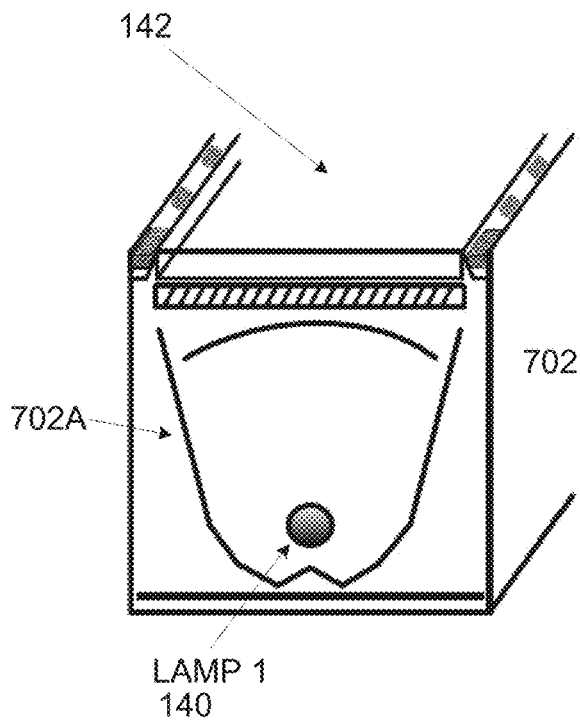 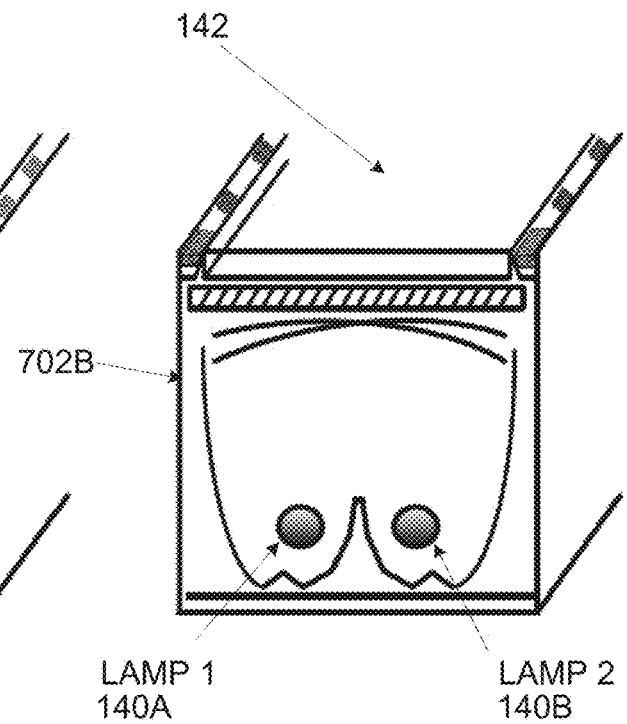
FIG. 7A   FIG. 7B
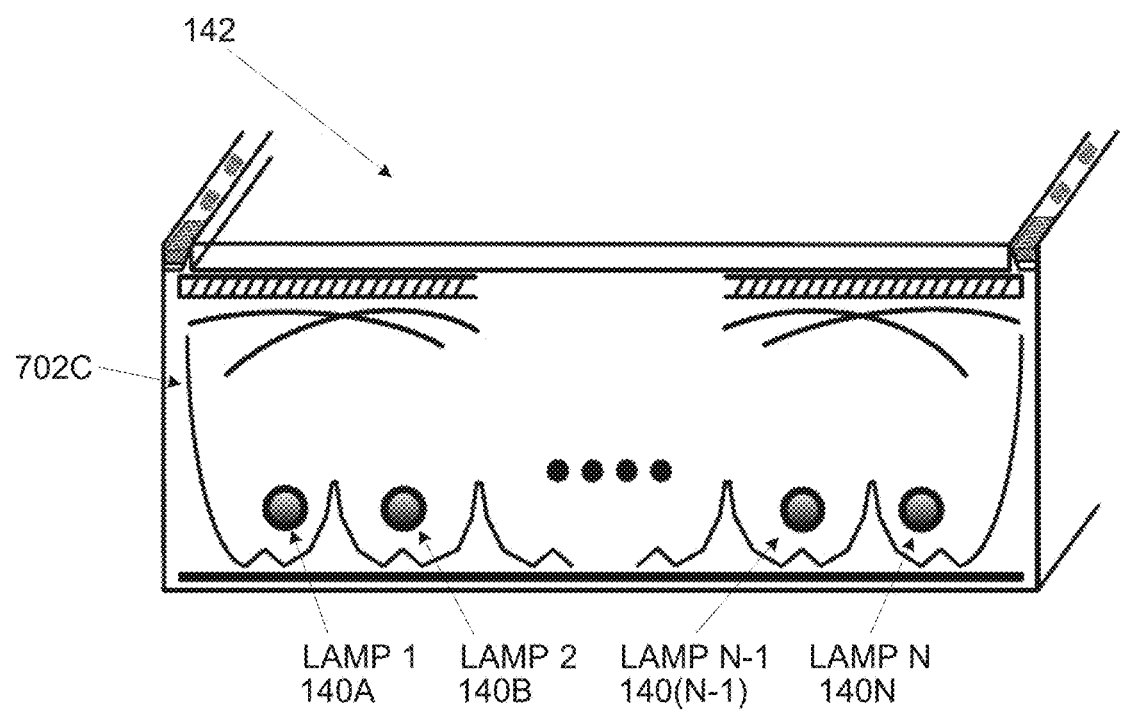
FIG. 7C

INTENSE PULSE LIGHT (IPL) APPARATUS UTILIZING A PULSE FORMING NETWORK (PFN)

RELATED APPLICATIONS

This application is a US Continuation of PCT Patent Application No. PCT/IL2019/050066 having international filing date of Jan. 16, 2019 which claims the benefit of priority under 35 USC § 119(e) of U.S. Provisional Patent Application No. 62/626,200 filed on Feb. 5, 2018. The contents of the above applications are all incorporated by reference as if fully set forth herein in their entirety.

FIELD AND BACKGROUND OF THE INVENTION

The present invention, in some embodiments thereof, relates to an Intense Pulse Light (IPL) apparatus and, more particularly, but not exclusively, to an IPL apparatus utilizing a Pulse Forming Network (PFN) for emitting a plurality of light pulse sequences for one or more IPL treatments.

IPL treatments are widely used for a plurality of procedures, mainly cosmetic and/or aesthetic treatments, for example, hair removal, skin pigmentation lesions treatment, vascular (vein) treatment, skin rejuvenation and/or the like. The IPL treatments are also common for treating dermatologic diseases such as acne and/or the like.

The IPL technology uses a high-powered energy source delivering intense, visible, broad-spectrum pulses of light, generally in a spectral range of 400 to 1200 nm (nanometer). Xenon flash lamps may typically be used for IPL treatments as they may produce high output bursts of broad spectrum. The resulting light has a spectral range that targets specific structures and chromophores (e.g. melanin in hair, or oxyhemoglobin in blood vessels) that are heated to destruction and reabsorbed by the body.

The IPL shares some similarities with laser treatments, in that they both use light to heat and destroy the target. But unlike lasers that use a single wavelength (color) of light which typically matches only one chromophore, and hence only one condition, IPL uses a broad spectrum that when used with filters, allows it to be used against several conditions. The spectrum may be further adjusted by selecting an appropriate filter that matches a specific chromophore.

SUMMARY OF THE INVENTION

According to a first aspect of the present invention there is provided an intense pulse light (IPL) apparatus utilizing a pulse forming network (PFN) for generating a plurality of light pulse sequences, comprising:
  A treatment unit comprising one or more lamps adapted to emit a plurality of light pulses towards a treatment face of the IPL apparatus.
  A PFN.
  A control unit adapted to operate the PFN to generate a regulated energized pulse to the one or more lamps. The regulated energized pulse having a desired multi-level voltage waveform with a maximum voltage level and a minimum voltage level which is in a range of 30-50 percent of the maximum voltage level.
Wherein rapidly varying heat is induced by a sequence of the plurality of light pulses emitted by the lamp(s) according to the multi-level voltage waveform.
  Constructing the multi-level voltage waveform with the low voltage level segments in the range of 20%-40% of the maximal highest voltage level segment may allow creating a heat profile having a relatively high heat level over the treatment area during the entire pulse length (bias) while applying dynamic and rapidly varying heat pulses to the treatment area during the high voltage level segments. Such heat profile may be highly effective for a plurality of IPL treatments, for example, hair removal, skin pigmentation lesions treatment, vascular (vein) treatment, skin rejuvenation and/or the like. The effectivity of the heat profile results from the fact that the human cells may be highly susceptible to extreme and rapid heat variations which may thus destroy the cells. Moreover, the relatively high voltage level of the low voltage level segments (20%-40% of the maximal voltage) may prevent cooling of the treatment area between the high voltage level segments which may significantly reduce the energy required to heat the treatment area again during a succeeding high voltage level segment of the following pulse. Furthermore, due to the reduced required energy, the voltage level of the high voltage level segments may be significantly reduced and as result little and typically no current and/or voltage regulation may be required for the energy discharged from the capacitor units thus facilitating the use of simple and/or low cost electrical regulators.

According to a second aspect of the present invention there is provided a method of using an intense pulse light (IPL) apparatus utilizing a pulse forming network (PFN), comprising:
  Operating, at a base unit of an IPL apparatus, the PFN to drive a regulated energized pulse having a desired multi-level voltage waveform with a maximum voltage level and a minimum voltage level which is in a range of 30-50 percent of the maximum voltage level.
  Generating a ready indication indicating the PFN is ready to discharge the regulated energized pulse to one or more of the lamps adapted to emit a plurality of light pulses towards a treatment face of a treatment unit of the IPL apparatus.
  Operating, in response to a trigger event, the PFN to discharge the regulated energized pulse, the trigger event is initiated by a user of the IPL apparatus after placing the treatment face on a treatment area.
  Wherein rapidly varying heat is induced on the treatment area by a sequence of the plurality of light pulses emitted by one or more of the lamps according to the multi-level voltage waveform.

In an optional implementation form of the first and/or second aspects, the control unit is adapted to operate the PFN to generate the multi-level voltage waveform with a first lamp pre-heating pulse having a voltage level which is in a range of 40-75 percent of the maximum voltage. Constructing the lamp pre-heating pulse to lead the multi-level voltage waveform of the regulated energized pulse may prevent the treatment area from experiencing and/or suffering a thermal shock. The lamp pre-heating pulse may also prevent a thermal shock to the lamp itself, in particular to the lamp(s)' electrodes thus significantly extending longevity of the lamp(s).

In a further implementation form of the first and/or second aspects, the PFN comprises a plurality of capacitor units adapted to store a plurality of charges in a plurality of working voltages, the control unit is adapted to operate a plurality of switches in a sequenced order, each of the plurality of switches is adapted to couple a respective one of the plurality of capacitor units to one or more electrical regulators to form the regulated energized pulse. The capacitor units of the PFN may be optimal for accumulating high energy and releasing this energy over a significantly short time interval to drive the lamp(s) which may translate this high energy to emit high intensity light pulses. The high intensity light pulses may induce highly dynamic and intensive heat levels (heat pulses) to the treatment area which are highly suitable for a plurality of IPL treatments. The control unit may further operate the regulator(s) and switch(es) to create the desired multi-level voltage waveform for the regulated energized pulse adapted for a specific IPL treatment, a specific patient, a specific treatment area characteristic and/or the like.

In a further implementation form of the first and/or second aspects, one or more of the lamps is a Xenon pulse lamp. The Xenon pulse lamp may be highly suitable for a plurality of the IPL treatments and is capable of emitting the high intensity light pulse when driven with the regulated energized pulse generated by the PFN.

In an optional implementation form of the first and/or second aspects, an asymmetrically shaped reflector is disposed around a plurality of the lamps having a cylindrical shape. The asymmetrically shaped reflector is disposed around a longitudinal axis the plurality of lamps to improve an even illumination distribution of the plurality of light pulses over the treatment face. The reflector is asymmetrically disposed around the longitudinal axis of each of the plurality of lamps such that:
  A low reflection surface of the reflector extending to a height of each lamp is disposed along a side of the longitudinal axis of each lamp facing another lamp of the plurality of lamps.
  A high reflection surface of the reflector extending above the height of each lamp is disposed along a side of the longitudinal axis of each lamp facing away from any other one of the plurality of lamps.

While improving direction of the light pulses energy towards the treatment face and/or improving a uniform distribution of the light pulses over the treatment face, the asymmetric reflector may prevent one or more of the lamps to directly illuminate one or more other lamps thus preventing overheating of the lamps and significantly improving longevity of the lamps.

In a further implementation form of the first and/or second aspects, the IPL apparatus is constructed of a treatment unit and a base unit, the treatment unit comprises the treatment face, the one or more lamps and a front-end controller, the base unit comprises the PFN and the control unit. Wherein the base unit drives the regulated energized pulse to the treatment unit through a primary wired interface electrically coupling the PFN to the lamp(s) and the front-end controller communicates with the control unit through one or more wireless communication channels. The two part design of the IPL apparatus may significantly ease usage of the IPL apparatus during the IPL session as the treatment unit which is light, relatively small and typically ergonomically shaped may allow the user to easily move, maneuver and/or apply the treatment face to the treatment area(s). The wireless communication channel(s) used for communication between the base unit and the treatment may significantly reduce complexity of the cabling means required to connect the treatment unit to the base unit and thus make the IPL apparatus less cumbersome for use. Employing the wireless communication channel(s) may further reduce complexity, cabling material and labor thus reducing cost of the IPL apparatus.

In an optional implementation form of the first and/or second aspects, the treatment unit comprises a power circuit adapted to convert power from the regulated energized pulse for providing power to the treatment unit. Generating power for the treatment unit components from the regulated energized pulse may further simplify the design of the IPL apparatus as a separate power cable dedicated for providing power to the treatment unit may be removed thus reducing cabling material and labor costs and hence reducing the cost of the IPL apparatus.

In an optional implementation form of the first and/or second aspects, the base unit provides power to the treatment unit through an auxiliary wired interface electrically coupling a power source of the base unit to a power circuit of the treatment unit. The base unit may provide the power to the treatment unit components through a separate auxiliary cable which may be significantly light due to the significantly low energy it delivers to the treatment unit components.

In an optional implementation form of the first and/or second aspects, The IPL apparatus comprises an extended base unit adapted to drive a respective one of a plurality of regulated energized pulses through a respective one of a plurality of a plurality of primary wired interfaces to each of a plurality of treatment units such as the treatment unit. The front-end controller of each of the plurality of treatment units communicates with the control unit of the extended base unit through one or more wireless communication channels. The multi treatment units IPL system may provide a fully independent operational environment to each of the treatment units since each of the plurality of treatment units receives its respective regulated energized pulse over a dedicated primary wired interface connecting the PFN at the extended base unit to the treatment unit's lamp(s). Communication between the font-end controllers of the plurality of treatment units and the control unit may be conducted over the wireless interface(s) to reduce complexity and/or excessive wiring and thus making use of each of the treatment units less cumbersome and more efficient. Such a multi treatment units IPL system may be highly beneficial for professional IPL caregivers who may use it to treat simultaneously a plurality of patients and/or treat simultaneously multiple treatment areas of one or more patients. The multi treatment units IPL system having a single base unit may have a significantly lower cost than a plurality of IPL apparatuses used to conduct the simultaneously treatment. Moreover, the multi treatment units IPL system may be less complex, occupy smaller room space and consume significantly less power than the plurality of IPL apparatuses.

In an optional implementation form of the first and/or second aspects, the treatment face is at least partially enclosed by a sharpened perimeter edge raised above the treatment face. Marking the treatment area may allow the user to easily identify the areas which were treated during previous cycles of the IPL session and efficiently place the treatment face over a treatment area selected for the current cycle. The sharpened perimeter edge may be an efficient low cost solution for applying such markings. Moreover, the markings applied by the sharpened perimeter edge are a result of the pressure applied by the sharpened perimeter edge to the skin around the treatment area. The markings are therefore temporary and may vanish after a short time.

In an optional implementation form of the first and/or second aspects, the treatment face is at least partially enclosed by a color applying perimeter edge raised above the treatment face. Applying the color to mark the treatment area may significantly improve accuracy of the markings and optionally improve visibility of the markings to the user. The color of the markings may optionally be invisible in the visible light spectrum and may be made visible to the user when illuminated with a light of a respective spectral range, for example, Ultra Violet (UV) light.

In an optional implementation form of the first and/or second aspects, the IPL apparatus comprises one or more light sources for illuminating a colored pattern applied to a treatment area by the color applying perimeter edge. The markings may be applied using a special color which is not visible in visible light spectrum. The light source(s), for example, UV light source(s) may therefore be used to illuminate the treatment area(s) with light in an appropriate spectrum, for example, UV light to make the markings visible to the user.

In a further implementation form of the first and/or second aspects, the control unit is adapted to verify proper attachment of the treatment face to the treatment area by determining a proximity of the treatment face to the treatment area based on analysis of sensory data obtained from a pair of photodiodes each deployed and adapted to capture a reflection of light emitted by one or more respective light sources deployed near the treatment face. Verifying the placement of the treatment face over the treatment area may allow for optimal placement and most effective impact of the IPL treatment thus significantly improving the IPL treatment and potentially reduce the number of IPL treatment cycles and/or sessions.

In an optional implementation form of the first and/or second aspects, the control unit is adapted to adjust the multi-level voltage waveform according to a skin color identified by analyzing sensory data obtained from one or more of the photodiodes. Adjusting the multi-level voltage waveform of the regulated energized pulse according to the skin color may allow controlling the intensity, pattern and/or duration of the light pulses and hence of the heat induced to the treatment area. This may allow generating the multi-level voltage waveform for an optimal IPL treatment parameters selected according to the identified skin color while avoiding inflicting damage to the treatment area.

In an optional implementation form of the first and/or second aspects, the control unit is adapted to adjust the multi-level voltage waveform according to one or more treatment area characteristics, for example, a skin color, a hair color, a hair type and/or the like. One or more of the treatment area characteristics are identified by analyzing one or more images obtained from one or more imaging sensors deployed to depict a treatment area. Adjusting the multi-level voltage waveform of the regulated energized pulse according to the other treatment area characteristics may significantly selection of the IPL treatment parameters since classification of the treatment area may be significantly improved.

In an optional implementation form of the first and/or second aspects, the IPL apparatus comprises a test area shaped to receive and accommodate the treatment face of the treatment unit, the control unit is adapted to evaluate one or more light emission attributes of one or more of the lamps by analyzing sensory data received from a plurality of light sensors exposed to the plurality of light pulses emitted by the one or more lamp while the treatment unit is placed in the test area. Testing the lamp(s) may allow identification of the operational state of the lamp(s) to identify faulty and/or damaged lamp(s). Moreover, identifying the actual operational state of the lamp(s) may allow extended usage of the lamp(s) beyond the operational period and/or operational stress indicated by a manufacturer of the lamp.

In an optional implementation form of the first and/or second aspects, the plurality of light sensors is deployed in the test area along a longitudinal axis of the lamp(s) to capture the plurality of light pulse in a plurality of locations along the longitudinal axis. The control unit is adapted to analyze the sensory data to identify one or more of the light emission attributes for the plurality of locations along the longitudinal axis. Placing the light sensors along the longitudinal axis of the lamp(s) may allow efficient characterization of the light emission attribute(s) of the lamp(s) at a plurality of locations along the lamp(s), in particular locations known to present degradation in such light emission attribute(s), for example, the end(s) of the longitudinal axis.

In an optional implementation form of the second aspect, one or more of the lamps are tested by operating the PFN to drive a test regulated energized pulse to the one or more lamps while the treatment unit is located in a test area of the IPL apparatus shaped to receive and accommodate the treatment unit and evaluating one or more light emission attributes of one or more of the lamps by analyzing sensory data received from a plurality of sensors deployed in the test area along a longitudinal axis of one or more of the lamps and exposed to the plurality of light pulses emitted by the lamp(s) according to the multi-level voltage waveform of the test regulated energized pulse. Testing the lamp(s) prior to the IPL session may assure that the session is conducted with fully operational lamp(s) thus potentially significantly improving results of the IPL session. Moreover, the test regulated energized pulse may be adjusted to generate light pulses which are optimal for testing the light emission attribute(s) of the lamp(s).

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a schematic illustration of an exemplary IPL apparatus utilizing a PFN for emitting a plurality of light pulse sequences, according to some embodiments of the present invention;

FIG. 2A is a schematic illustration of an exemplary PFN used by an IPL apparatus, according to some embodiments of the present invention;

FIG. 2B is a graph chart of exemplary sensory data captured by a light sensor of an IPL apparatus adapted to a capture light emitted by proximity lights source(s) of the IPL apparatus, according to some embodiments of the present invention;

FIG. 3A, 3B and FIG. 3C are graph charts of exemplary regulated energized pulses having desired multi-level voltage waveform patterns adapted to drive an IPL lamp of an IPL apparatus, according to some embodiments of the present invention;

FIG. 4 is a capture of a spectrometer image of a light emission spectrum generated by an IPL lamp driven with an exemplary regulated energized pulse having a desired multi-level voltage waveform pattern, according to some embodiments of the present invention;

FIG. 5A, FIG. 5B and FIG. 5C are graph charts of exemplary pairs of regulated energized pulses having desired multi-level voltage waveform patterns adapted to drive a pair of IPL lamp of an IPL apparatus, according to some embodiments of the present invention;

FIG. 6A and FIG. 6B are schematic illustrations of exemplary pairs of regulated energized pulses having synchronized and alternating multi-level voltage waveform patterns adapted to drive a pair of IPL lamp of an IPL apparatus, according to some embodiments of the present invention;

FIG. 7A, FIG. 7B and FIG. 7C are schematic illustrations of exemplary reflectors of exemplary IPL apparatuses having one, two and a plurality of IPL lamps respectively, according to some embodiments of the present invention;

FIG. 8A is a schematic illustration of a simulation of illumination distribution of light emitted by a pair of IPL lamps of an exemplary IPL apparatus having reflectors adapted to reflect the emitted light, according to some embodiments of the present invention;

FIG. 8B is a graph chart of a simulation of heat distribution of heat induced by light emitted by two IPL lamps of an exemplary IPL apparatus having reflectors adapted to reflect the emitted light, according to some embodiments of the present invention;

FIG. 9A is a schematic illustration of a treatment unit of an exemplary IPL apparatus utilizing a PFN, according to some embodiments of the present invention;

Figure 9A:
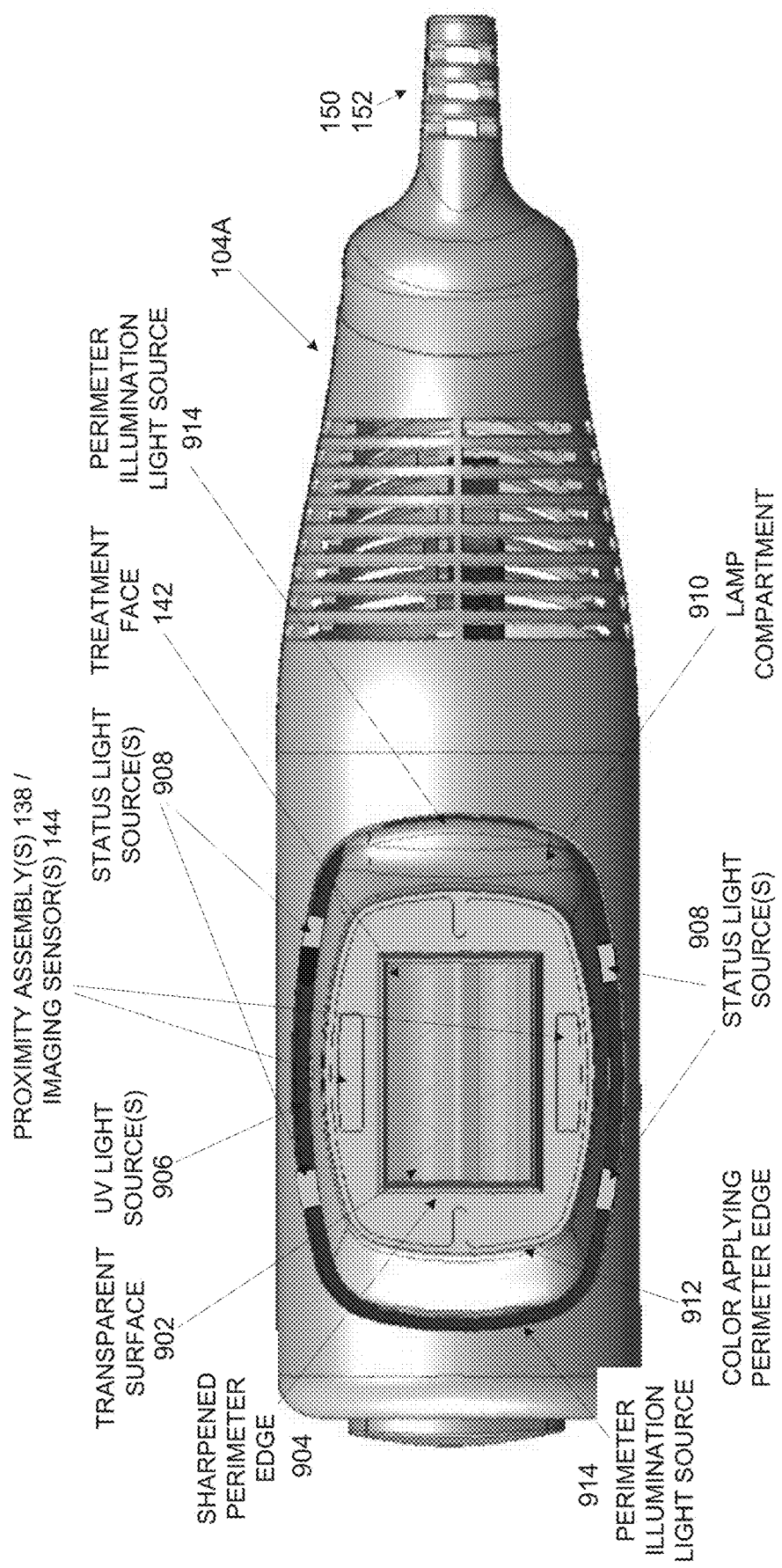
Figure 9B:
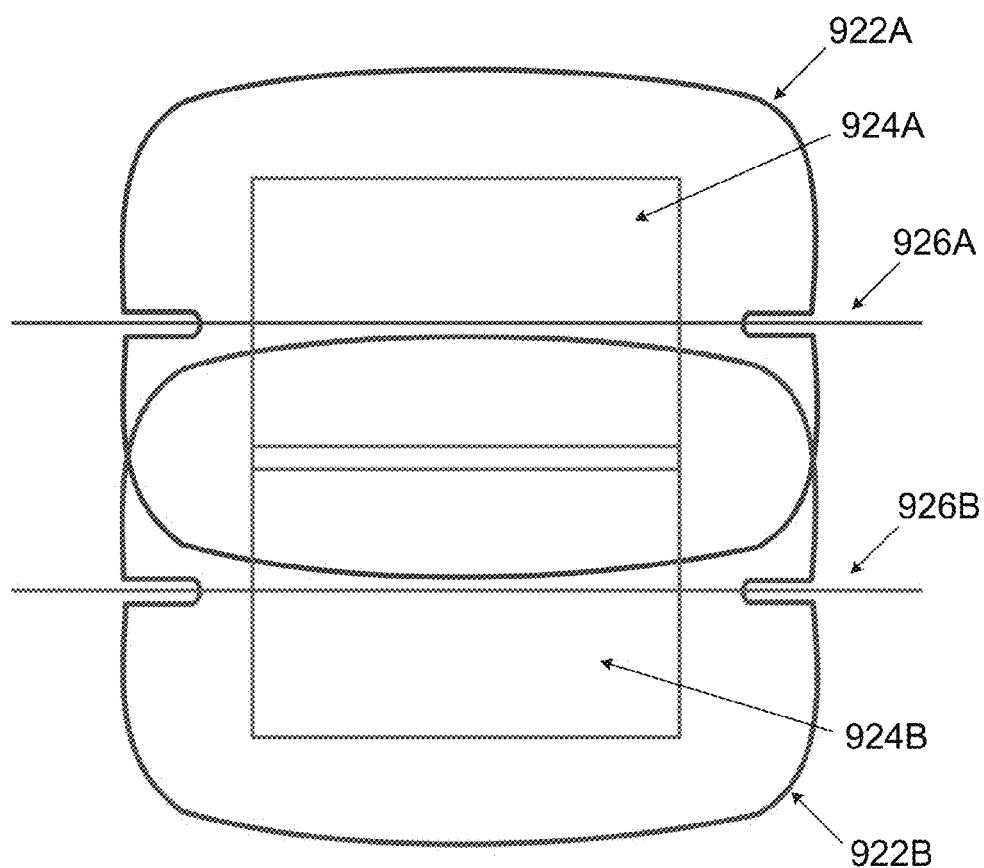
Figure 9C:
Figure 11A:
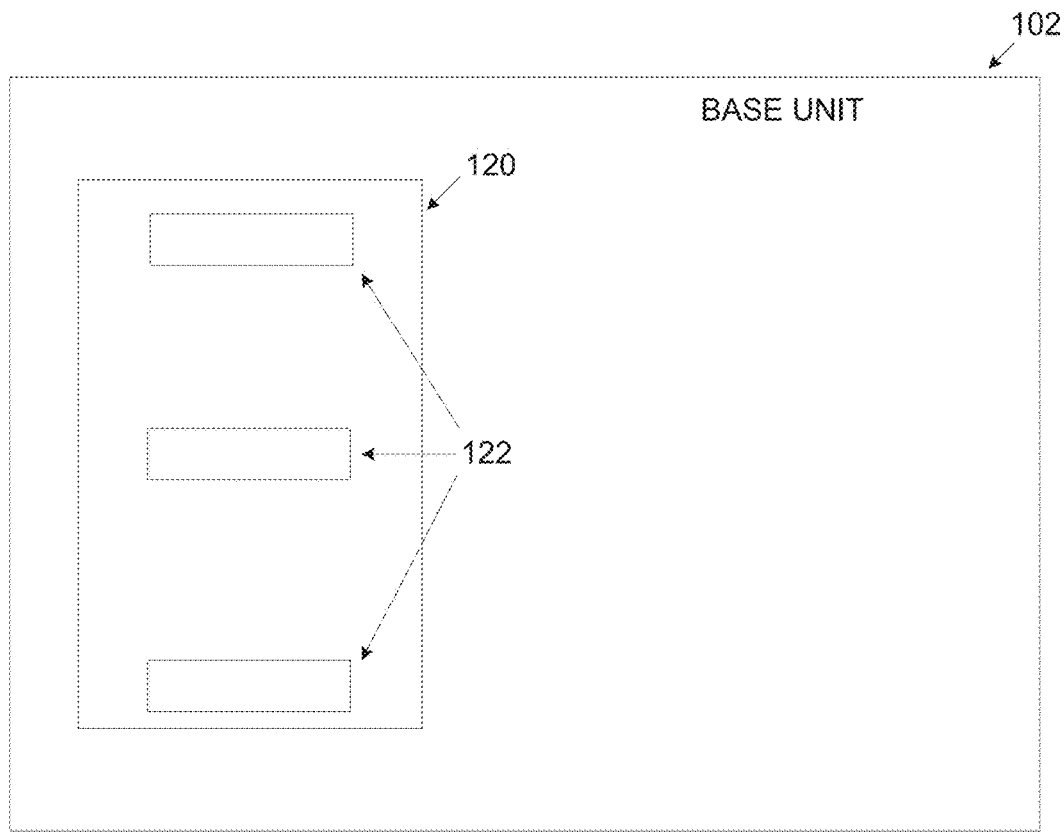
Figure 11B:
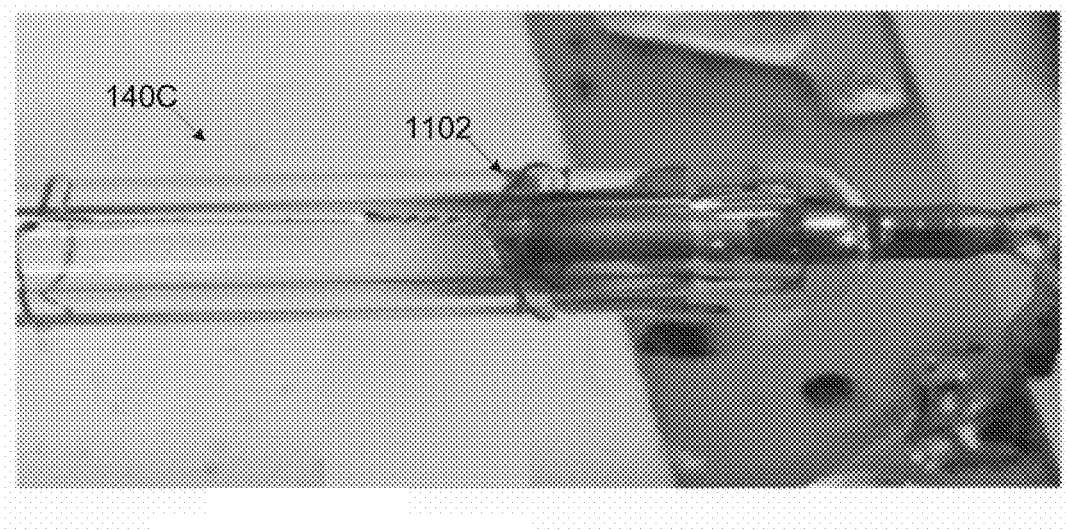
Figure 12:
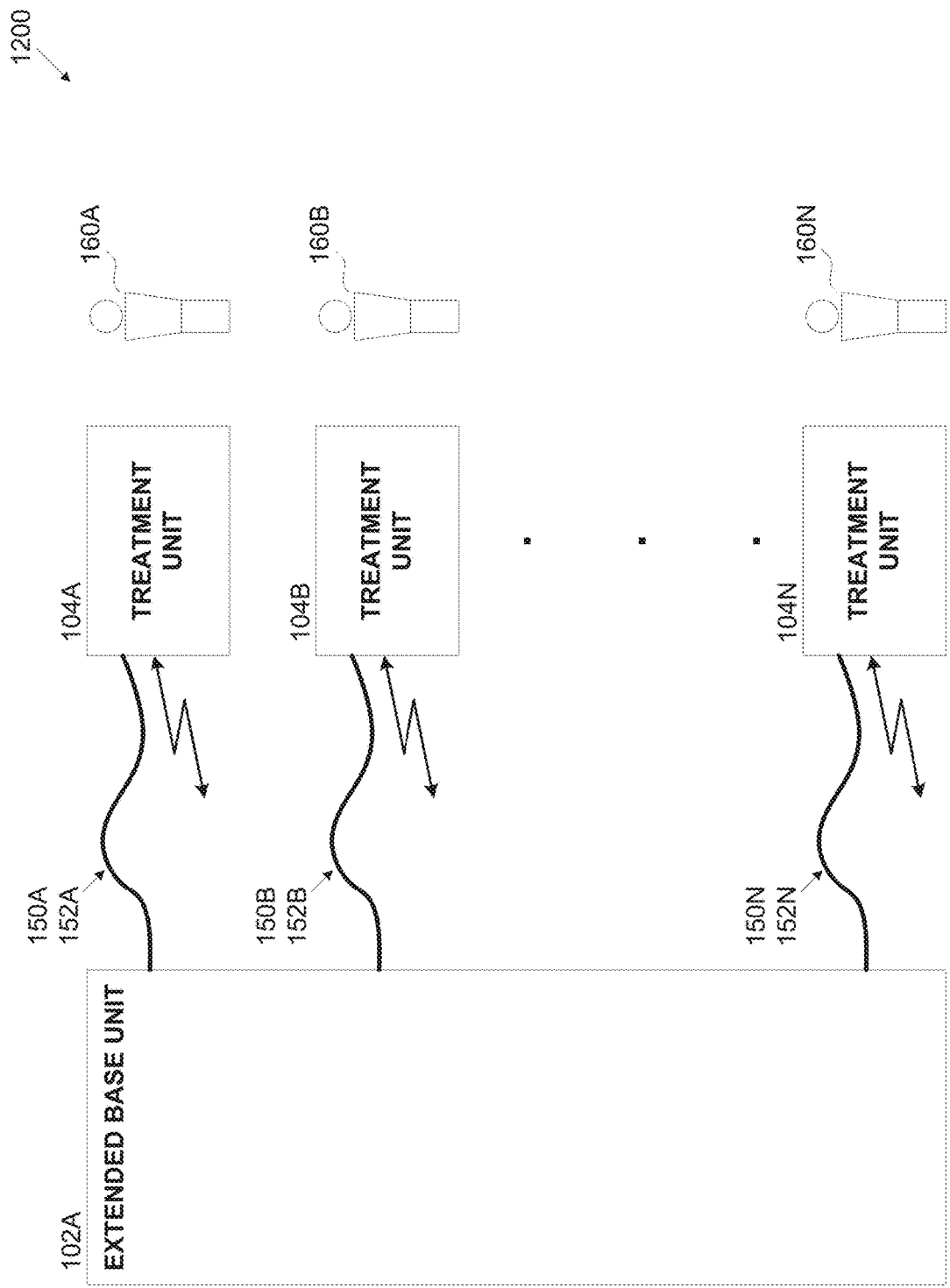
Figure 13:
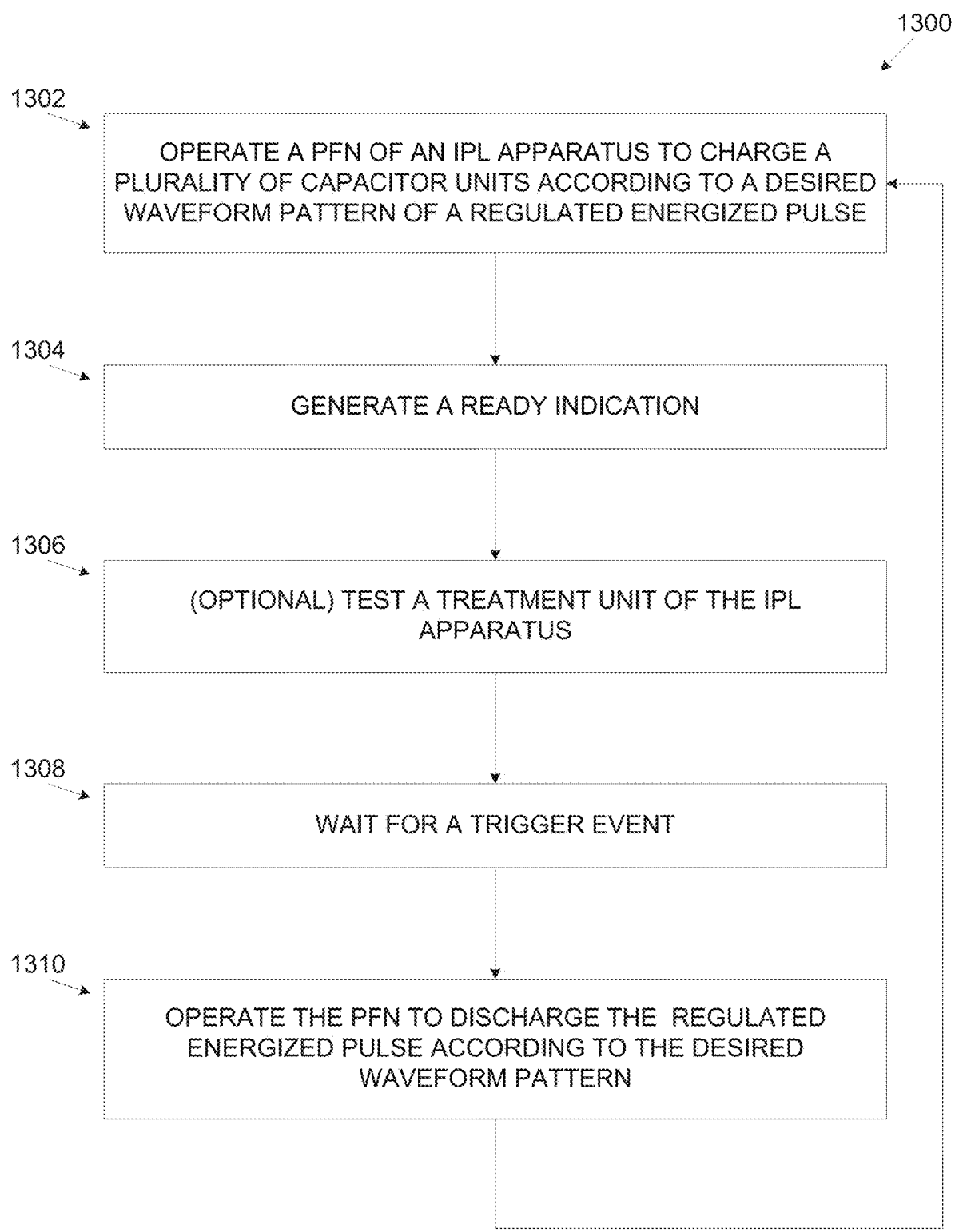

FIG. 9B and FIG. 9C are a schematic illustration and a picture of exemplary treatment area color markings applied by a color applying element of a treatment unit of an IPL apparatus utilizing a PFN, according to some embodiments of the present invention;

FIG. 10A, FIG. 10B, FIG. 10C and FIG. 10D are captures of a treatment unit of an exemplary IPL apparatus utilizing a PFN, according to some embodiments of the present invention;

FIG. 11A is a schematic illustration of an exemplary test area of an IPL apparatus utilizing a PFN, according to some embodiments of the present invention;

FIG. 11B is an image capture of a damaged lamp of an IPL apparatus;

FIG. 12 is a schematic illustration of an exemplary IPL apparatus utilizing a PFN and comprising a plurality of treatment units captures of a treatment unit, according to some embodiments of the present invention; and FIG. 13 is a flow chart of an exemplary process executed by an IPL apparatus utilizing a PFN for an IPL treatment, according to some embodiments of the present invention.

DESCRIPTION OF SPECIFIC EMBODIMENTS OF THE INVENTION

The present invention, in some embodiments thereof, relates to an IPL emitting apparatus and, more particularly, but not exclusively, to an IPL utilizing a PFN for emitting a plurality of light pulse sequences one or more IPL treatments.

According to some embodiments of the present invention there are provided an IPL apparatus and processes for using the IPL apparatus for a plurality of IPL treatments, for example, hair removal, skin pigmentation lesions treatment, vascular (vein) treatment, skin rejuvenation and/or the like. The IPL treatments are based on exposing a treatment area, specifically a skin segment of a patient to high intensity light pulses which induce highly focused heat energy to the treatment area thus destroying the target. The IPL apparatus therefore uses one or more IPL lamps, for example, a Xenon flash lamp and/or the like to deliver the high energy pulses (in a spectral range of 400 to 1200 nm) to the treatment area. To emit sequences of such high energy light pulses suitable for the IPL treatments, the lamp(s) may be fed with high energy regulated energized pulses having a desired multi-level voltage waveform adapted for the specific IPL treatment. In particular, the IPL apparatus adjusts the energy regulated energized pulses to excite the lamp(s) to induce heat to the treatment area with a heat profile having a significantly high heat level throughout the duration of the pulse with highly dynamic and rapidly varying heat levels.

The IPL apparatus comprises a Pulse Forming Network (PFN) which includes a plurality of modules each comprising a capacitor unit for storing and building high energy charges. The PFN, specifically the modules may further include switches and electrical regulator to allow control of the energy discharged from the capacitor units and for regulating the discharge. The capacitor units may accumulate extremely large electrical energy, for example, in the range of 80V-400V over a comparatively long time and then sequentially release the accumulated electrical energy, under control of a control unit of the IPL apparatus, to create the regulated energized pulse in the form of a relatively square high energy pulse of comparatively short duration.

The control unit of the IPL apparatus may apply one or more IPL algorithms adapted to operate the PFN to construct the regulated energized pulse characterized by a multi-level voltage waveform pattern having multiple high voltage level segments and corresponding low voltage level segments. The multi-level voltage waveform may be created such that the high voltage level segments are gradually decreasing to avoid overheating the treatment area. This may be easily implemented since the high voltage level segments may gradually decrease as result of the capacitor units discharge process throughout the duration of the regulated energized pulse. The regulated energized pulse may be further constructed such that the low voltage level segments of the multi-level voltage waveform are in a range of 20%-40% of the maximal high voltage level segment. However, the regulated energized pulse may be constructed such that during the entire pulse (i.e. the high voltage level segments and the low voltage level segments) a minimal voltage level is maintained which is above a certain level, for example, 100 Vdc to maintain the lamp(s) in their excited and operational state. For example, the maximum voltage of the highest voltage level segment may be about 400 Vdc and the low voltage level segments of the multi-level voltage waveform may therefore be in the range of 80 Vdc to 160 Vdc. As such, the lamp(s) may emit highly intense light to keep a relatively high mean temperature level throughout the entire pulse length of the regulated energized pulse (i.e. the high voltage level segments and the low voltage level segments) while dynamically inducing rapidly varying highly increased heat levels (heat pulses) during the high voltage level segments.

Optionally, the control unit operates the PFN to generate the regulated energized pulse with equal duration and/or equal voltage level of the high voltage level segments and equal duration and/or equal voltage level of the low voltage level segments. Adjusting the multi-level voltage waveform patterns of the regulated energized pulse such that the high voltage level segments and the low voltage level segments have a significantly similar duration may significantly increase the difference between the voltage extremes. Meaning that the difference between the maximal high voltage level during the high voltage level segments and the minimal low voltage level during the low voltage level segments. Increasing the difference may increase the dynamic heat variations thus increasing effectivity of the IPL session.

The control unit of the IPL apparatus may adjust one or more parameters of the multi-level voltage waveform to set the desired pattern for the regulated energized pulse, for example, a number of pulses, a power of each of the pulses, a level of the high voltage level and/or of the low voltage level of each pulse, a duration of the high voltage level and/or of the low voltage level segment of each pulse, a high and/or low current level of each pulse and/or the like. The operational parameters may be set according to the IPL treatment type (e.g. hair removal, pigmentation, rejuvenation, vascular, etc.) and/or according to one or more characteristics of the treatment area, for example, a skin color (e.g. dark, light, etc.), a hair color (e.g. dark, light, etc.), a hair type (e.g. thick, thin, etc.) and/or the like.

The control unit of the IPL apparatus may further construct the regulated energized pulse to include a first lamp pre-heating pulse leading the multi-level voltage waveform. The voltage level of the lamp pre-heating pulse may be set to 40%-75% of the maximal high voltage level segment of the regulated energized pulse. For example, assuming the maximum voltage of the highest voltage level segment is about 400 Vdc, the voltage level of the lamp heating pulse may therefore be in the range of 160 Vdc to 300 Vdc.

As mentioned before, the IPL apparatus may include a plurality of lamps to cover larger treatment areas. In such case the regulated energized pulse driven to each of the lamps may be synchronized and/or alternating compared to the regulated energized pulse(s) driven to the other lamps. The synchronized operation of the lamps where all lamps are simultaneously driven with regulated energized pulses having similar multi-level voltage waveform patterns may significantly increase the dynamic heat variations since the low and high voltage extremes are increased and/or lowered respectively. The alternating operation of the lamps where consecutive lamps are driven with regulated energized pulses having opposite multi-level voltage waveform patterns may significantly increase the treatment area treated during each IPL cycle.

The IPL apparatus may typically comprise a base unit which is a stationary unit and a treatment unit which is mobile and may be hand held, grasped, gripped and/or the like by a user, for example, a responsible person, the patient, a caregiver, a cosmetics technician and/or the like maneuvering the treatment unit to one or more treatment areas of the patient. The base unit may comprise elements, mechanisms and/or components required for generating regulated energized pulses having a desired multi-level voltage waveform pattern, specifically the PFN and the control unit. The treatment unit comprises the lamp(s) fed with the regulated energized pulses to emit the light pulses which induce heat to the treatment area. The regulated energized pulses may be delivered from the base unit, i.e. from the PFN to the lamp(s) primary wired interface adapted to deliver high energy electrical current.

The treatment unit and the base unit may communicate with each other over one or more wired and/or wireless communication channels. The treatment unit may include one or more batteries to provide power to the electronic components of the treatment unit. However, the treatment unit may optionally receive its power (for its electronic components) from the base unit through an auxiliary wired interface.

The IPL apparatus, in particular, the treatment unit may include one or more reflectors constructed from one or more highly reflective materials shaped, configured, located and/or positioned to increase efficiency of the illumination distribution of the light pulses emitted by the lamp(s). For example, the reflector(s) may significantly improve energy utilization of the light pulses by directing the emitted light towards the treatment area. The reflector(s) may further improve an even illumination distribution of the light pulses. Moreover, in case the IPL apparatus comprises a plurality of lamps, the reflector(s) may be shaped asymmetrically around for the exterior lamps facing an end of the treatment face to reflect the light emitted from the lamps towards the treatment area. Optionally, the exterior lamps are positioned asymmetrically, i.e. off center with respect to the center of their respective reflector surface to improve light direction towards the treatment face.

The treatment unit includes a treatment face which is placed over the treatment area of the patient. The treatment face may typically include a protection surface covering the lamp(s) to prevent direction contact of the treatment area with the lamp(s) which may be extremely hot. The protection surface may be at least partially transparent to allow the light pulses generated by the lamp to pass through the protection surface towards the treatment area. The protection surface may further include a filter to filter at least part of the spectrum of the light pulses.

Optionally, the treatment face is at least partially enclosed by a sharpened perimeter edge disposed around at least part of the treatment face. The sharpened perimeter edge may typically be slightly raised above the treatment face such that while placing the treatment face on the treatment area, the sharpened perimeter edge may apply pressure around the treatment area to mark the edges of the treatment area treated during a current IPL session cycle. Additionally and/or alternatively, the treatment face is at least partially enclosed by a color applying perimeter edge disposed around at least part of the treatment face. When placing the treatment face over the treatment area, the color applying perimeter edge may apply color, for example, an Ultra Violet (UV) ink and/or the like to the treatment area's edges thus marking the treatment area treated during a current IPL session cycle. In such embodiments, the treatment unit may further include one or more light sources, for example, a UV lamp, a UV LED and/or the like to illuminate the treatment area and make the UV ink markings visible to the user.

Optionally, the control unit verifies proper attachment of the treatment face to the treatment area by determining proximity of the treatment face from the treatment area. This may be done by analyzing sensory data received from one or more light sensors, for example, photodiodes placed near the treatment face which are adapted to capture reflection of light from the treatment area which is illuminated by one or more proximity light sources, for example, a LED and/or the like.

Additionally and/or alternatively, the treatment unit may include one or more imaging sensors, for example, a camera, an infrared camera, a thermal sensor and/or the like for capturing one or more images of the treatment area. The control unit may analyze the sensory data received from the light sensor(s) and/or the image(s) received from the imaging sensor(s) to identify one or more characteristics of the treatment area, for example, the skin color, the hair color, the hair type and/or the like. The control unit may operate the PFN to generate the regulated energized pulse according to the identified treatment area characteristics. Moreover, based on the analysis of the sensory data received from one or more of the light sensors and/or analysis of the image(s) captured by the imaging sensor(s), the control unit may identify one or more characteristics of the surface in proximity to the treatment face, for example, a texture, a material and/or the like. Based on the identified characteristics, the type of the surface may be identified.

The IPL apparatus, specifically the base unit may further include a test area shaped to receive and accommodate the treatment unit, specifically the treatment face for testing the treatment unit, in particular for testing the lamp(s). The base unit may include one or more light sensors deployed in and/or around the test area to capture light emitted by the lamp(s) while the treatment face is placed in the test area. Sensory data captured by the light sensor(s) may be analyzed to identify values of one or more emission attributes of the lamp(s), for example, level, intensity, distribution, spectrum and/or the like. Based on the identified light emission attribute(s), the operational status of the lamp(s) may be evaluated.

Optionally, the base unit is configured as an extended base unit adapted to operate as a master device supporting a plurality of slave treatment units.

The IPL apparatus and IPL algorithms described herein the present invention may present significant benefits compared to existing devices, systems and/or methods for IPL treatments. Some of the traditional IPL apparatuses may generate regulated energized pulses. However, such IPL apparatuses may typically construct the voltage waveform of the regulated energized pulses to have high voltage level segments and corresponding low voltage level segments which are dropped to the bare minimum voltage required to maintain the lamp(s) in their active state. The voltage level of the low voltage level segments may therefore be significantly low.

In contrast, the IPL apparatus presented herein is adapted to construct the multi-level voltage waveform with the low voltage level segments in the range of 20%-40% of the maximal highest voltage level segment. This may allow creating a heat profile having a relatively high heat level over the treatment area during the entire pulse length (bias) while applying dynamic and rapidly varying heat pulses to the treatment area during the high voltage level segments. Such heat profile may be highly effective for a plurality of IPL treatments, for example, hair removal, skin pigmentation lesions treatment, vascular (vein) treatment, skin rejuvenation and/or the like. The effectivity of the heat profile results from the fact that the human cells may be highly susceptible to extreme and rapid heat variations which may thus destroy the cells. Therefore by subjecting the cells to a relatively high heat over the treatment area for the entire pulse length and simultaneously applying the highly dynamic, rapid and major heat pulses, the cells may be effectively destroyed. Furthermore, by constructing the regulated energized pulses with equal duration and voltage level for the high voltage level segments and equal duration and voltage level for the low voltage level segments the heat profile of the heat induced to the treatment area may be further improved. This is because the dynamic heat variation may be maximal thus significantly more effective for the IPL treatment(s). The improved heat profile may allow for more effective destruction of the cells and may therefore significantly reduce the number of treatment cycles during the IPL session.

Moreover, the relatively high voltage level of the low voltage level segments may prevent cooling of the treatment area between the high voltage level segments. This may significantly reduce the energy required to heat the treatment area again during a succeeding high voltage level segment of the following pulse. The voltage level of the high voltage level segments may therefore be significantly reduced thus requiring lower capacity capacitor units which may significantly reduce the capacitor units cost. Additionally and/or alternatively, reducing the voltage level of the high voltage level segments may allow construction of longer regulated energized pulses which may improve the IPL treatment session. Also the reduced voltage level may reduce the stress applied to the capacitor units which may improve longevity and/or endurance of the capacitor units.

Furthermore, as the voltage level of the high voltage level segments may be reduced, little and typically no current and/or voltage regulation may be required for the energy discharged from the capacitor units thus allowing the use of simple and/or low cost electrical regulators. In case of the multiple lamps IPL apparatus, the regulated energized pulse driven to each of the lamps may be synchronized and/or alternating compared to the regulated energized pulse(s) driven to the other lamps. As the heat induced by the light pulses emitted by all the lamps is combined, when synchronizing the regulated energized pulse driven to the plurality of lamps, the energy required from each lamp may be significantly reduced thus further allowing the use of capacitor units. Additionally and/or alternatively, when driving the lamps with alternating regulated energized pulses, the treatment area may significantly increase thus requiring fewer cycles during a given IPL session and shortening the treatment session.

In addition, constructing the lamp pre-heating pulse to lead the multi-level voltage waveform of the regulated energized pulse may prevent the treatment area from experiencing and/or suffering a thermal shock as may be experienced when using the existing IPL apparatus since the lamp pre-heating pulse may induce a relatively moderate heat level to the treatment area. The lamp pre-heating pulse may also prevent a thermal shock to the lamp itself, in particular to the lamp(s)' electrodes thus significantly extending longevity of the lamp(s).

The two part design of the IPL apparatus comprising the base unit and the treatment unit may significantly ease usage of the IPL apparatus during the IPL session. The treatment unit which is light, relatively small and typically ergonomically shaped may allow the user to easily move, maneuver and/or apply the treatment face to the treatment area(s). The more massive elements of the IPL apparatus, specifically the PFN and the power supply(s) may be integrated in the base unit which may be stationary during the IPL session. The wireless communication channel(s) used for communication between the base unit and the treatment may significantly reduce complexity of the cabling means required to connect the treatment unit to the base unit and thus make the IPL apparatus less cumbersome for use. Employing the wireless communication channel(s) may further reduce cabling costs, labor and complexity thus reducing costs of the IPL apparatus.

The uniquely designed and disposed reflectors may significantly increase the energy utilization of the light pulses to effectively induce heat over the treatment area. As the reflectors may reduce the lost energy, the energy utilization is increased and lower capacity units may be used which may be charged with lower charging voltage. In case of the multiple lamps IPL apparatus, the asymmetric reflector may prevent one or more of the lamps to directly illuminate one or more other lamps. This may prevent overheating of the lamp(s) and may significantly improve longevity of the lamps.

In addition, marking the treatment area with the sharpened perimeter edge and/or with the color applying perimeter edge may allow the user to easily identify the areas which were treated during previous cycles of the IPL session and efficiently place the treatment face of the treatment unit over a treatment area selected for the current cycle.

Also, verifying that the treatment face properly attached to and placed at an effective distance from the treatment area may significantly improve the effect of the light pulses emitted by the lamp(s) for the IPL treatment(s). Moreover, preventing emission of the light pulses when the treatment face is not attached to the treatment area may prevent damage to the user and/or the patient, for example, direct high intensity glare to an eye and/or the like. Furthermore, identifying the surface type the treatment face is attached to and/or is in proximity to may allow verifying that the treatment face is indeed placed over a treatment area and not over objects which may have hazardous effects. In addition, analyzing the sensory data captured by the proximity sensor(s) and/or analyzing the image(s) captured by the imaging sensor(s) may allow effective and accurate adaptation of the IPL treatment, i.e. the multi-level voltage waveform of the regulated energized pulse according to the characteristics of the treatment area and/or of the patient.

Lastly, testing the lamp(s) by analyzing and evaluating their emission attribute(s) may allow identification of the operational state of the lamp(s) to identify faulty and/or damaged lamp(s) and indicate the user to replace it in order to increase the effectivity of the IPL treatment. Moreover, identifying the actual operational state of the lamp(s) may allow extended usage of the lamp(s) beyond the operational period and/or operational stress indicated by a manufacturer of the lamp. For example, the manufacturer may typically state a certain number of light pulses the lamp(s) may endure. For integrity and/or reputation reasons the manufacturer may intentionally state a number of light pulses which is lower than the actual number the lamp(s) may endure. By identifying the actual operational state of the lamp(s), in case the lamp(s) are determined to be fully operational, the lamp(s) may be used beyond the limitations stated by the manufacturer. In another example, the manufacturer may state a number of maximum energy light pulses the lamp(s) may endure. However, in many cases the user may not operate the lamp(s) to their maximum energy mode but rather to a lower energy operation mode. As such the lamp(s) may be used for longer periods and/or for higher numbers of light pulses.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages.

The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s).

In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Several embodiments of an IPL apparatus employing a PFN to generate sequences of light pulses for aesthetic and/or medical treatment are described hereinafter. However the presented embodiments should not be construed as limiting. A person skilled in the art may implement, construct, arrange and/or produce the IPL apparatus and/or parts thereof through multiple other implementations, structures, shapes, production methods and the like which employ the same concepts described throughout the present invention. Moreover, while one or more of the IPL apparatus's features may be described hereinafter for one or more of the embodiments, one or more of the features may be applicable for other embodiments as well even when not explicitly stated.

Figure 1:
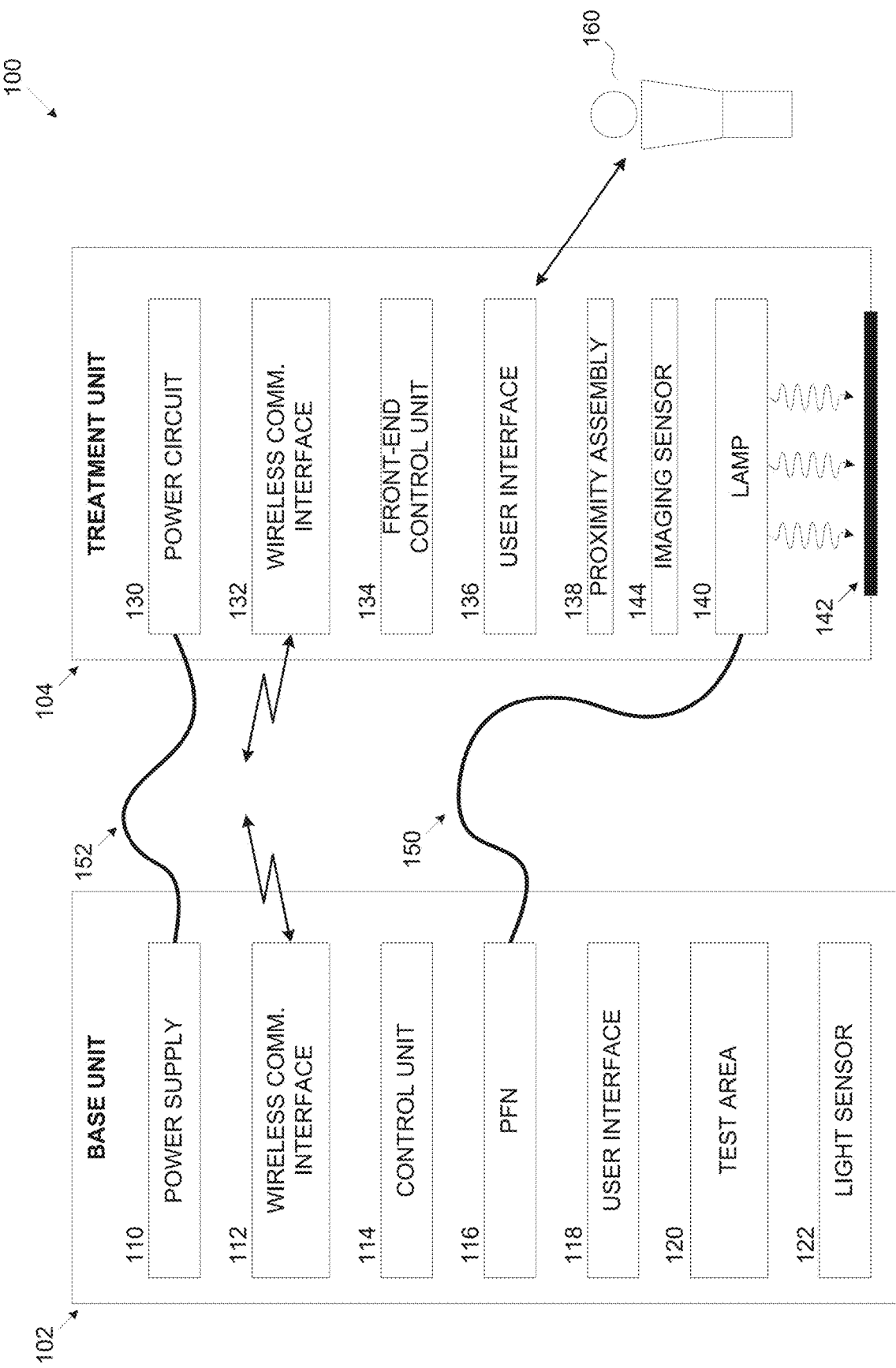

Referring now to the drawings, FIG. 1 is a schematic illustration of an exemplary IPL apparatus utilizing a PFN for emitting a plurality of light pulse sequences, according to some embodiments of the present invention. An exemplary IPL apparatus 100 may be for generating sequences of light pulses applied to one or more treatment areas of a patient during one or more aesthetic and/or medical treatments, specifically, hair removal, skin pigmentation lesions, skin rejuvenation and/or the like. The IPL apparatus 100 includes a base unit 102 and a treatment unit 104. While in some embodiments of the present invention the base unit 102 and the treatment unit may be integrated as a single device, typically the base unit 102 and the treatment unit 104 are separated from each other. In such constructions, the base unit 102 may typically be a stationary unit comprising elements, mechanisms and/or components required for generating regulated energized pulses having a desired multi-level voltage waveform pattern. The regulated energized pulses may be driven to feed one or more lamps 140 adapted for IPL treatment which generate sequences of light pulses corresponding to the multi-level voltage waveform pattern of the regulated energized pulses. The sequences of light pulses emitted by the lamp(s) 140 may induce heat on the treatment area(s) in levels adapted for the treatment. In order to induce high heat level (temperature) sufficient for the IPL treatments, the lamp(s) 140 may be driven with significantly high energy regulated energized pulses. The treatment unit 104 comprising the lamp(s) 140 may be a mobile unit which may be held, grasped, gripped and/or the like by a user 160, for example, a responsible person, the patient, a caregiver, a cosmetics technician and/or the like maneuvering the treatment unit 104 to one or more treatment areas of the patient. The IPL treatment may comprise of a plurality of treatment cycles where during each cycle the light pulses are applied to another treatment area.

The base unit 102 may include a power supply 110, a communication interface, specifically a wireless communication interface 112, a control unit 114, and a PFN 116. The base station 102 may optionally include a user interface 118, a test area 120 and one or more light sensors 122.

The power supply 110 may include one or more electric circuits designed, adapted and/or configured to provide electrical power to the PFN as well as to one or more of the electronic components of the base unit 102. The power supply 110 may generate high power sources delivering significantly high current and high voltage for charging capacitive elements of the PFN 116. The power supply 110 may further provide one or more power rails, for example, a +3.3 Direct Current (DC) Voltage (Vdc), a +5 Vdc, a +12 Vdc and/or the like. The power supply 110 may also provide power to one or more electronic components of the treatment unit 104, for example, one or more of the power rails through an auxiliary wired interface 152 coupling the power supply 110 to the treatment unit 104.

The power supply 110 may include a power circuit adapted to receive power from a power grid, for example, 110 Vac/60 Hz, 220 Vac/50 Hz and/or the like and convert them to one or more power rails. The IPL apparatus 100 may thus include a power cord connecting the power supply 110 to a power outlet. Optionally, the power supply 110 includes one or more power circuits adapted to utilize one or more batteries to generate the power rails required for the electronic unit(s) of the IPL apparatus 100. The power supply 110 may further include a charging circuit for recharging the batteries from the power grid. In case the power supply 110 is capable of utilizing the battery(s), the base unit 102 may include a battery compartment adapted to receive and accommodate one or more batteries. The battery compartment may be fitted with contacts to connect the poles of the battery(s) to the power circuit of the power supply 110. The battery compartment may include a detachable cover that may be opened and closed during replacement of the battery(s).

The PFN 116 may include a plurality of modules, each comprising a capacitor unit electrically wired for connection to a load, specifically the lamp(s) 140 via an electrical regulator and a switch. The PFN 116 may be electrically coupled to the lamp(s) 140 through a primary wired interface 150 adapted to deliver high energy electrical current, specifically the regulated energized pulses.

Figure 2A:
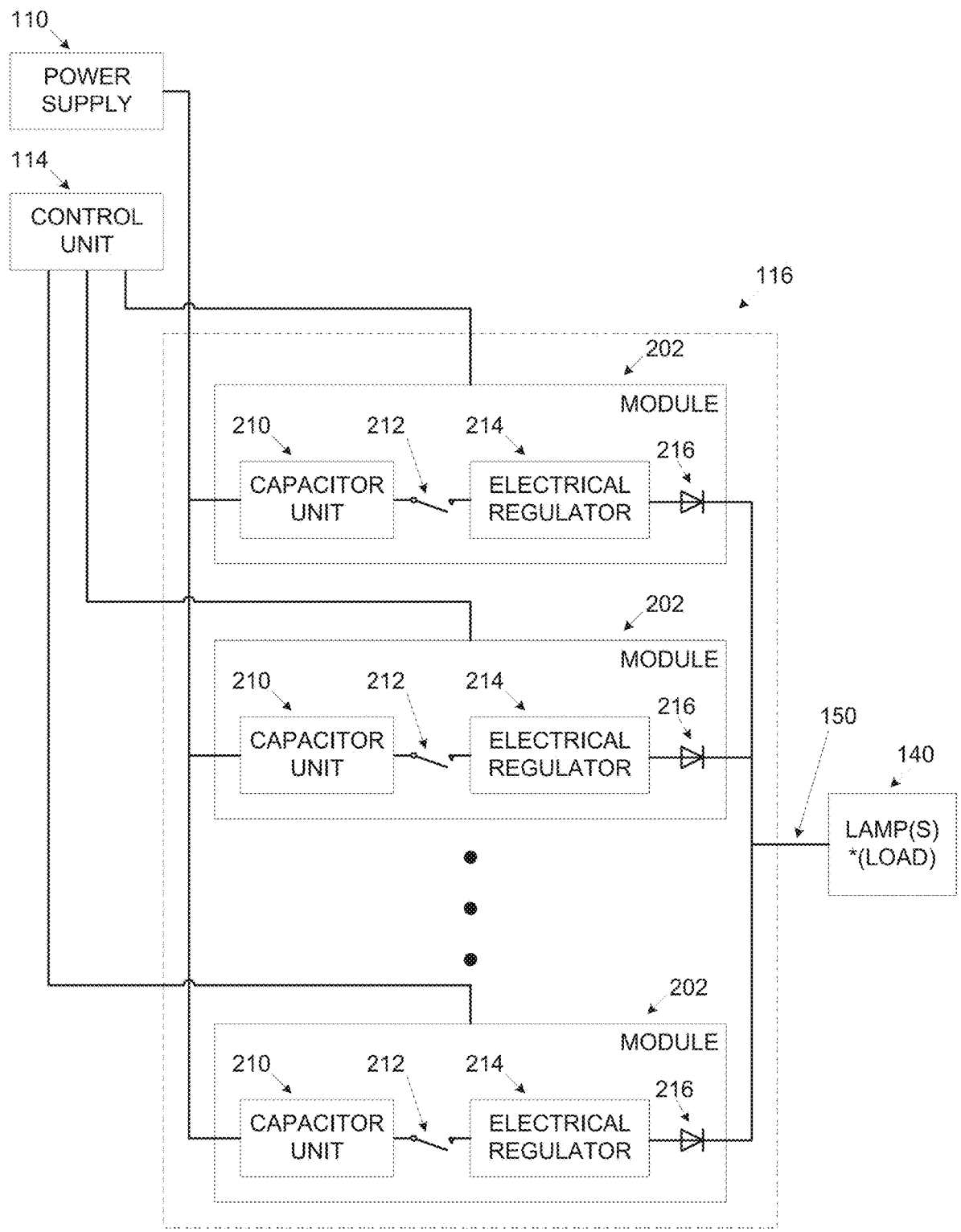

Reference is now made to FIG. 2A, which is a schematic illustration of an exemplary PFN used by an IPL apparatus, according to some embodiments of the present invention. An exemplary PFN 116 of an IPL apparatus such as the IPL apparatus 100 may which is part of a base unit such as the base unit 102 may include a plurality of modules 202. Each of the modules 202 comprises a capacitor unit 210 electrically wired for connection to a load, specifically a lamp such as the lamp(s) 140 via an electrical regulator 214 and a switch 212. The capacitor units 210 may be fed with an input charge by a power supply such as the power supply 110. The power supply 110 may charge the capacitor units 210 with energy which is ten times or even more of the input charge. In use, the capacitor units 210 of the PFN 116 accumulate electrical energy over a comparatively long time and then sequentially release the accumulated electrical energy, under the control of a control unit such as the control unit 114, in the form of a relatively square pulse of comparatively short duration.

The capacitor units 102 are adapted to output common or different output voltage levels. When the capacitor units 210 are charged to a common voltage level, the PFN 116 may energize the lamp(s) 140 with a pulse having a substantially uniform regulated voltage. However, when the capacitor units 210 are charged to different voltage levels, the PFN 116 may energize the lamp(s) 140 by producing and delivering a plurality of sequential regulated charges that form a patterned energizing pulse having a regulated multi-level voltage waveform where, as used herein, energizing means supplying with electrical power. The multi-level voltage waveform may have various shapes, such as a square waveform, a Gaussian waveform and/or a thin integrated circuit or any other non-sinusoidal waveform, such as rectangular waveforms, ramp waveforms, triangle waveforms, spiked waveforms and/or saw-tooth waveforms.

The discharge level of each capacitor unit 210 is correlated with a voltage regulation level of the respective electrical regulator 214. For example, the electrical regulator 214 may bring a voltage level of the discharged energy to the lamp(s) 140 (load) to about 90% of the minimum input discharged voltage level. Optionally, the current of the discharged energy is higher than the feed current driven by the power supply 110 to charge the capacitor units 210.

The capacitor units 210 may be charged by the one or more insolated power sources provided by the power supply 110. In some embodiments of the present invention, multiple capacitor units 210 may share a single power source provided by the power supply 110 such that the single power source is used to charge the multitude of capacitor units 210. In other embodiments, one or more of the capacitor units 210 may be charged by a dedicated power source provided by the power supply 110. In such embodiments, each power source of the power supply 110 may be adapted to the voltage level of the fed capacitor unit 102. As the voltage level of the charging power source and the capacitor units 210 may be adapted to the desired output load, less energy may be wasted during the charging of the capacitor units 102.

The modules 202 may be connected to a circuitry which allows simultaneously connecting some or all of the modules 202 to the lamp(s) 140 (load) for example, via a wired interface such as the primary wired interface 150. In such a manner, the output of the modules 202 may be combined to form a discharge having a higher current than the current that may be discharged by each of the modules 202 separately. The circuitry may connect the modules 202 in parallel so that the output thereof is an accumulation of high currents. It should be noted that as the output of each module 202 is regulated, the summed output is also regulated.

Additionally and/or alternatively, some or all of the modules 202 may be connected in a circuitry which allows summing the outputs thereof to increase the voltage of the discharge before energizing the lamp(s) 140 (load) for example, via the primary wired interface 150. In such a manner, the output of the modules 202 may be combined to form a discharge with a higher voltage than the voltage that may be discharged by each of the modules 202 separately. The circuitry may connect the output modules 202 in series (one after the other) such that the output thereof is an accumulation of voltages and a high voltage discharge may be applied to the lamp(s) 140. Again, it should be noted that as the output of each module 202 is regulated, the summed output is also regulated.

Optionally, a diode 216, such as an anti-reversing diode, is provided between the electrical regulator 214 and the lamp(s) 140 to keep the capacitor units 210 from becoming a load when each module 202 discharges a different charge.

Optionally, each capacitor unit 210 is connected to a local indicator or test circuit, which is set to indicate whether the respective capacitor unit 210 functions properly or not. Optionally, the indicator circuit comprises a status Light Emitting Diode (LED) that is active when the respective capacitor unit 210 operates properly. The LED(s) may be provided as part of the user interface 118 optionally provided by the base unit 102.

Each of the electrical regulators 214 which may be set to regulate voltage and/or current, for example a switching (electronic) regulator, an analog regulator and/or the like maintains a constant voltage level and/or current accordingly. The regulated voltage may be set automatically or selected by the control unit 114, as described herein after. Depending on the design, each electrical regulator 214 may be used to regulate one or more DC voltages and/or currents from the capacitor units 210. As the electrical regulator 214 maintains a constant voltage level and/or current, the output of each one of the modules 210, as received by the lamp(s) 140 (load), can be evaluated in advance.

All the electrical regulators 214 may be connected to the lamp(s) 140. It should be noted that as the charges discharged by the capacitor units 210 have known and constant voltages, the range of voltages which have to be regulated is limited and therefore low cost electrical regulators 214 which are set to regulate a limited dynamic range of Δ input voltage may be used. It should further be noted that Electromagnetic Interferences (EMC) may have a reduced effect on the PFN 116 since simultaneous and non-simultaneous operation of the electrical regulators 214 which are limited in their working output voltage level and/or designated power sources are used. Moreover, when the plurality of electrical regulators 214 is used, current flows to the lamp(s) 140, through each electrical regulator 214, in relatively short intervals. Thus, relatively thin wires and/or a small power devices and integrated circuit may be used to conduct the regulated charges to the lamp(s) 140.

Optionally, the capacitor unit 210 of some or all of the modules 202 is connected to a number of electrical regulators such as the electrical regulator 214. This may allow using capacitor units 210 with high voltage potential which have higher functionality duration.

Reference is made once again to FIG. 1.

The control unit 114 may include one or more processing devices, for example, a processor (homogenous or heterogeneous), a controller and/or the like. The control unit 114 may further include storage for storing code, data and/or the like. The storage may include one or more persistent and/or volatile devices, for example, a Read Only Memory (ROM) device, a Flash device, a hard drive, an attachable storage media, a random access memory (RAM) and/or the like. The processing device(s) may execute one or more software, firmware and/or middleware modules, for example, a process, an application, an agent, a utility, a service and/or the like to control operation of one or more components of the base unit 102. Wherein a software, firmware and/or middleware module refers to a plurality of program instructions executed by a processor such as the processing device(s) from a program store such as the storage.

The wireless communication interface 112 may be used to facilitate communication between the base unit 102 and the treatment unit 104. The wireless communication interface 112 may include one or more interfaces supporting one or more communication protocols, in particular close range communication protocols, for example, Wireless Local Area Network (WLAN), Bluetooth, Near Field communication (NFC) and/or the like. For example, the control unit 114 may use the wireless communication interface 112 to communicate with the treatment unit 104, for example, to indicate the PFN 116 is ready to discharge its energy charge.

The base unit 102 may optionally include a user interface 118 which may be controller by the control unit 114 for interacting with the user 160 operating the IPL apparatus 100. The user interface 118 may include one or more status indication lights, for example, an ON/OFF indication light, a malfunction (failure) indication light, an operational status indication light and/or the like.

For example, the status indication lights may include the status LED indicating the operational status of the capacitor units 210. The user interface 118 may also include one or more control switches, for example, a button, a switch, a lever and/or the like, for example, an ON/OFF button, a reset button, an operation mode selection dial, a test mode button and/or the like. The operation mode selection dial, for example, may be used to select one or more parameters of the multi-level voltage waveform to set the desired pattern for the regulated energized pulse. The parameters of the multi-level voltage waveform may be set according to the current IPL treatment, for example, the type of the IPL treatment, one or more characteristics of the patient, in particular the skin of the patient and/or the like. For example, for an IPL hair removal treatment, the multi-level voltage waveform may be set according to the skin type of the patient and/or according to the hair type. Darker skin and/or thicker hair may require intensive heat, i.e. high temperature for a longer duration and may therefore require higher energy regulated energized pulse for a longer period of time. Lighter skin on the other hand may be damaged by excessive heat and may thus require high peak energy pulses having for short time durations. Such high peak energy short time durations pulses may also be highly efficient for light vascular and/or pigmentation IPL treatments. In another example, the test mode button may set the IPL apparatus 100 to test mode and/or the normal operation mode.

The user interface 118 may further include a display, for example, a Liquid Crystal Display (LCD) and/or the like allowing the control unit 114 to present information to the user, for example, status information, maintenance information and/or the like. The screen may further be a touch screen to allow the user to interact with the control unit 114. The user interface 118 may also include a sound interface, for example, a speaker, a buzzer, a piezoelectric device and/or the like for generating one or more sound indications, for example, a ready sound indication, a failure sound indication and/or the like.

The base unit 102 may optionally include a test area 120 shaped to receive and accommodate the treatment unit 104 for testing the treatment unit 104, in particular for testing the lamp(s) 140. One or more light sensors 122 may be deployed in the test area 120 to capture light emitted by the lamp 140 while the treatment unit 104 is placed in the test area 120 and the control unit 114 operates the PFN 116 to generate the regulated energized pulses and drive them to the lamp(s) 140. The control unit 114 may collect, obtain and/or receive sensory data from the light sensor(s) 122 and analyze the sensory data to identify values of one or more of the light emission attributes of the lamp 140, for example, the level, the intensity, the distribution, the spectrum and/or the like. Based on the identified light emission attribute(s), the control unit 114 may evaluate the operational status of the lamp(s) 140 and determine whether the lamp(s) 140 is operating properly or not.

The treatment unit 104 may include a power circuit 130, a communication interface, specifically a wireless communication interface 132, a front-end control unit 134, a user interface 136, and one or more lamps 140, specifically IPL lamp(s) 140 adapted to emit light towards a treatment face 142 for IPL treatment.

The power circuit 130 may include one or more electric circuits designed, adapted and/or configured to provide electrical power to one or more of the electronic components of the treatment unit 104. The power circuit 130 may receive one or more of the power rails, for example, the +3.3 Vdc, the +5 Vdc, the +12 Vdc and/or the like from the power supply 110 through the auxiliary wired interface 152 coupling the power supply 110 to the power circuit 130. Optionally, the power circuit 130 includes one or more power circuits adapted to utilize one or more batteries to generate the power rail(s) for one or more of the electronic units of the treatment unit 104. In case the power circuit 130 is capable of utilizing the battery(s), the treatment unit 104 may include a battery compartment adapted to receive and accommodate one or more batteries. Moreover, in such case the auxiliary wired interface 152 is removed. The battery compartment may be fitted with contacts to connect the poles of the battery(s) to the power circuit(s) of the power circuit 130. The battery compartment may include a detachable cover that may be opened and closed during replacement of the battery(s).

Optionally, the power circuit 130 includes one or more electric circuits designed, adapted and/or configured to generate the power rail(s) for the electronic component(s) of the treatment unit 104 from the regulated energized pulses driven by the PFN 116 over the primary wired interface 150. The lamp(s) 140 may have a minimal heating voltage which is required to excite the lamp 140 to enter an operational state and start emitting light. Since exciting the lamp(s) 140 into operation may be time consuming, the PFN 116 may be operated by the control unit 114 to continuously drive at least a minimal current to the lamp(s) 140 over the primary wired interface 150 to keep the lamp(s) 140 in the operational state. The power circuit 130 may therefore generate the power rail(s) for the electrical components of the treatment unit 104 from the continuously available current driven to the lamp(s) 140 through the primary wired interface 150.

The front-end control unit 134 may include one or more processing devices, for example, a processor (homogenous or heterogeneous), a controller and/or the like. The front-end control unit 134 may further include storage for storing code, data and/or the like. The storage may include one or more persistent and/or volatile devices, for example, a ROM device, a Flash device, a hard drive, an attachable storage media, a RAM and/or the like. The processing device(s) may execute one or more software, firmware and/or middleware modules for controlling operation(s) of one or more components of the treatment unit 104, for communicating with the control unit 114 and/or the like.

The wireless communication interface 132 may be used to facilitate one or more communication channels between the treatment unit 104 and the base unit 102. The wireless communication interface 112 may support one or more communication protocols, in particular close range communication protocols, for example, WLAN, Bluetooth, NFC and/or the like.

Naturally, the wireless communication interface 132 and the wireless communication interface 112 employ the same communication protocol(s) to establish the communication channel(s) between the base unit 102 and the treatment unit 104. The communication channels may be used by the treatment unit 104, specifically the front-end control unit 134 and the base unit 102, specifically the control unit 114 to communicate with each other. The wireless communication channel(s) used for communication between the base unit 102 and the treatment unit may 104 significantly reduce complexity of the cabling means required to connect the treatment unit to the base unit and thus make the IPL apparatus less cumbersome for use. Employing the wireless communication channel(s) may also reduce the cabling required for connecting the treatment unit may 104 to the base unit 102 thus significantly reducing costs of materials and/or assembly of the IPL apparatus 100.

For example, the front-end control unit 134 may detect one or more user triggered events, for example, a trigger to apply the light pulses to the treatment area and transmit a trigger instruction to the control unit 114. In response the control unit 114 may operate the PFN 116 to generate the regulated energized pulse to the lamp(s) 140. In another example, the control unit 114 may transmit a ready massage to the front-end control unit 134 indicating that the PFN 116 is ready (i.e. the capacitor units 210 are sufficiently charged) to discharge the regulated energized pulse to the lamp(s) 140. In response the front-end control unit 134 may, for example, activate a ready indication light at the treatment unit 104.

The lamp(s) 140 may include one or more lamps, specifically lamps typically used for the IPL treatment(s), for example, a Xenon lamp and/or the like. The lamp(s) 140 are located, positioned, configured and/or adapted to emit light to the treatment face 142. The lamp(s) 140 may emit the light pulses in a pattern corresponding to the desired pattern of the desired multi-level voltage waveform of the regulated energized pulse fed by the PFN 116 under control of the control unit 114 to the lamp(s) 140. The lamp(s) may be located, placed and/or fitted in one or more lamp compartments which may include a transparent surface through which the light pulses emitted from the lamp(s) 140 may propagate (travel) towards the treatment area 142 while preventing direct contact with the lamp(s) 140. The transparent surface may optionally include a filter to filter out at least part of the spectrum of the light emitted by the lamp(s) 140. Typically the lamp(s) 140 are disposable and are optionally provided in one or more cartridges that may be replaced periodically.

The treatment unit 104 may therefore include one or more lamp cartridge compartments shaped to receive and accommodate one or more of the lamps 140. The lamp cartridge compartment(s) may include a detachable cover that may be opened and closed during replacement of the lamp(s) 140. The lamp cartridge compartment(s) may be fitted with contacts to connect the lamp(s)' poles to the wire contacts adapted to deliver the regulated energized pulses. The treatment face 142 may constitute an external face of the lamp compartment(s), and may optionally be part of the cartridge(s) hosting the lamp(s) 140.

The treatment unit 104 may further include one or more perimeter illumination light sources for illuminating the treatment area to assist the user 160 by providing the user 160 clear visibility of the treatment area during the IPL treatment session. The perimeter illumination light source(s) may be typically disposed, located and/or positioned around a perimeter of the treatment face 142 to effectively illuminate the treatment area.

The treatment unit 104 may optionally include a user interface 136 which may be controller by the front-end control unit 134 for interacting with the user 160 operating the IPL apparatus 100. The user interface 136 may include one or more status indication lights, for example, an ON/OFF indication light, an operational status indication light, a malfunction (failure) indication light and/or the like. For example, the status indication lights may include a ready indication light which may indicate that the PFN 116 is charged and ready to discharge the regulated energized pulse to the lamp(s) 140. Once the ready indication light is activated (e.g. ON, flashing, etc.), after placing the treatment face 142 over the treatment area, the user 160 may initiate a trigger event to instruct release of the regulated energized pulse to cause the lamp(s) 140 to emit the light pulses. The user interface 136 may also include one or more control switches, for example, a button, a switch, a lever and/or the like. For example, the user interface 136 may include a trigger button for triggering release of the regulated energized pulse from the PFN 116 to the lamp(s) 140. In another example, the reset button, the operation mode selection dial, the test mode button and/or the like may be incorporated in the user interface 136. The user interface 136 may further include a display, for example, an LCD and/or the like allowing the front-end control unit 134 to present information to the user, for example, status information, maintenance information and/or the like. The user interface 136 may also include a sound interface, for example, a speaker, a buzzer, a piezoelectric device and/or the like for generating one or more sound indications, for example, a ready sound indication (such as the ready indication light), a failure sound indication and/or the like. The front-end control unit 134 may communicate with the control unit 114 to transmit data input received from the user 160 through the user interface 136. The front-end control unit 134 may also receive data from the control unit 114 and present the received data to the user 160 through the user interface 136.

Optionally, the treatment unit 104 includes one or more proximity assemblies 138 comprising one or more proximity light sources, for example, a LED and/or the like coupled with respective light sensors, for example, a photodiode and/or the like which may be used to verify proper attachment and/or placement of the treatment face 142 over the treatment area. The proximity assembly(s) 138 may be deployed, located, positioned and/or adapted to monitor proximity, i.e. distance of the treatment face 142 from adjacent objects.

The treatment unit 104 may typically include at least two proximity assemblies 138 typically placed at opposing sides of the treatment face to verify proper attachment of the entire treatment face 142 to the treatment area. For example, the proximity assemblies 138 may be placed at the middle of opposite ends of the treatment face 142 thus facing each other. In another example, the proximity assemblies 138 may be placed at the two opposite corners of the treatment face 142 thus facing each other. The proximity light source(s) and the light sensor(s) may be selected, adapted and/or configured to operate in one or more light spectrums, for example, visible light, infrared, UV and/or the like.

Proximity of the treatment face 142 from the treatment area (or other objects) may be determined according to the level of light reflected from the treatment area (or other surface) when illuminated by light emitted from the proximity light sources. In order to create a known reference, the proximity light sources may be operated, for example, by the front-end controller 134 to emit light at different intensity levels which may be compared to identify and omit effects of external light source(s), for example, the sun, a lighting lamp and/or the like. By comparing the measured light intensity for the different intensity levels of the proximity light sources a bias level contributed by the external light source(s) may be identified, for example, by the front-end controller 134. To this end, the proximity light sources may employ one or more implementations. For example, the proximity light sensors may include an adjustable intensity light source which may be adapted to emit light at a plurality of intensity levels, for example, proportional to a current and/or voltage driven to the light source. In another example, the proximity light sensors may include multiple independent light sources, for example, two light sources which may be operated individually to emit the light at different intensities.

Figure 2B:
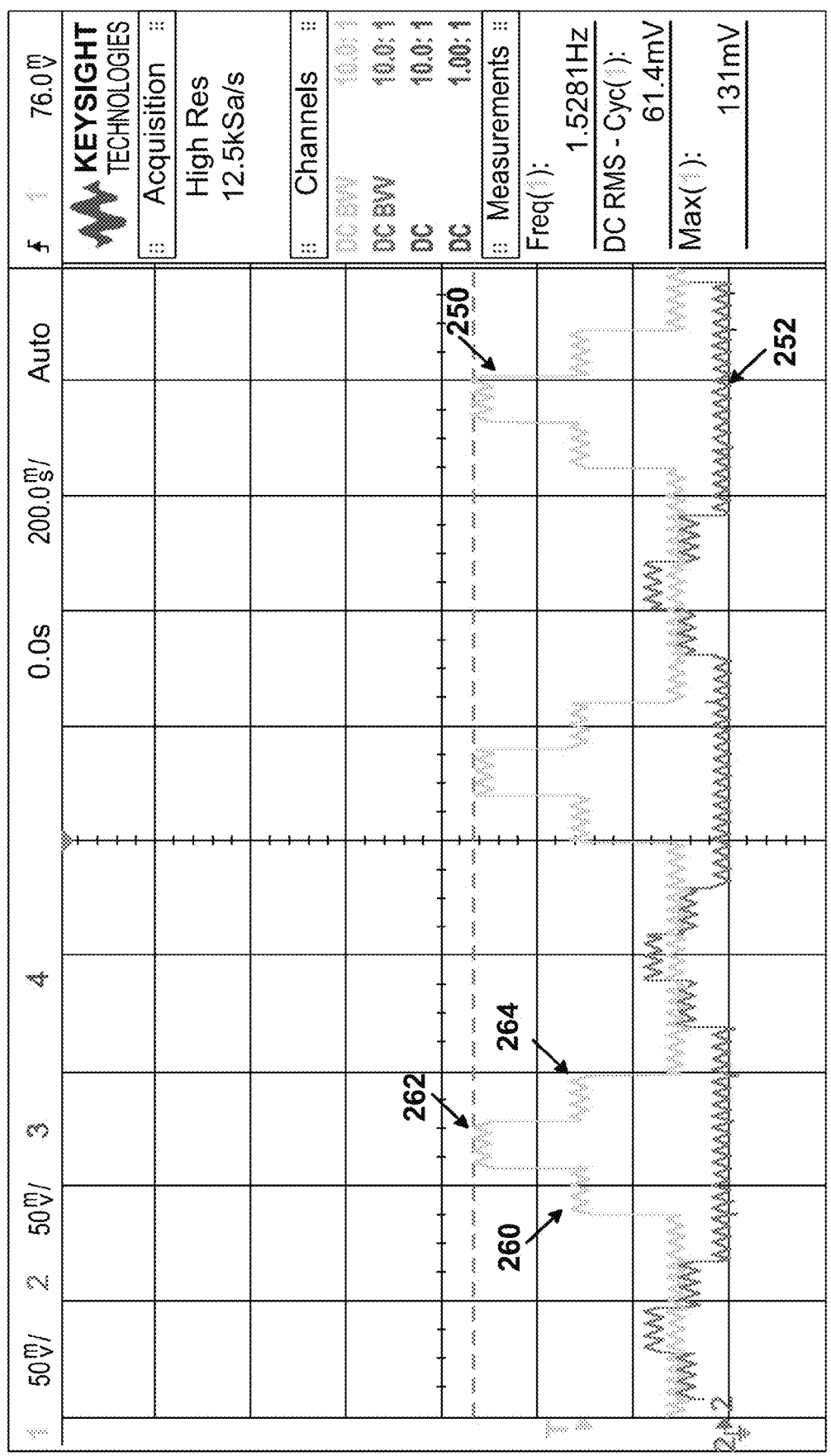

Reference is now made to FIG. 2B, which is a graph chart of exemplary sensory data captured by a light sensor of an IPL apparatus adapted to a capture light emitted by proximity lights source(s) of the IPL apparatus, according to some embodiments of the present invention. The graph chart presents exemplary graphs 250 (yellow) and 252 (green) expressing sensory data captured by a light sensor such as the light sensor of the assembly 138, for example, a photodiode. The graphs 250 and 252 present a voltage level generated by the photodiode in proportion to the light intensity detected by the photodiode. The graph 250 presents the voltage level indicative of the detected light intensity when the photodiode is in very close proximity to an object reflecting light emitted by one or more proximity light sources such as the proximity light source of the proximity assembly 138, for example, a LED. The graph 252 presents the voltage level indicative of the detected light intensity when no object is in proximity to the proximity light source(s) and hence little and/or no light is reflected towards the photodiode.

As seen in the graph 250, the light source(s) may be operated, for example, by the front-end controller 134 to emit a first light intensity level reflected by the level 260 in the graph 250. The front-end controller 134 may then operate the light source(s) to emit a second light intensity level reflected by the level 262 in the graph 250. The front-end controller 134 may further operate the light source(s) to emit a third light intensity level reflected by the level 264 in the graph 250. The graph 250 presents the voltage generated by the photodiode in response to detected light which is emitted from two LED proximity light sources. In such implementation, the level 260 may be generated by the photodiode in response to detection of the first light intensity level achieved by turning ON a first one of the two LEDs and turning OFF a second one of the two LEDs. The level 262 may be generated by the photodiode in response to detection of the second light intensity level achieved by turning ON both the first LED and the second LED. The level 264 may be generated by the photodiode in response to detection of the third light intensity level achieved by turning OFF the first LED and turning ON the second LED. In case the two LEDs are of the same type, the levels 260 and 264 may be significantly similar.

As evident, the pattern of the graph 252 may be very similar to pattern of the graph 250 with the exception that the voltage levels may be significantly lower since very little light may be reflected towards the photodiode since no object is located in proximity to the LEDs. The differences between the graphs 250 and 252 may be sued to determine the proximity of the proximity assembly 138 and hence of a treatment face such as the treatment face 142 to another object, specifically to the treatment area.

Reference is made once again to FIG. 1.

The front-end control unit 134 may collect, obtain and/or receive sensory data from the light sensor of the proximity assembly(s) 138 and analyze the sensory data to determine the distance of the treatment face 142 from the treatment area. The front-end control unit 134 may further analyze the sensory data provided by the light sensor(s) of the proximity assembly(s) 138 to identify one or more characteristics of the surface in proximity to the treatment face 142, for example, a texture, a reflection level, a material and/or the like. Based on the identified characteristics of the surface the front-end control unit 134 may identify and/or determine the type of surface the treatment face 142 is attached to and/or placed over. This may be used to verify the identified surface is indeed the treatment area and thus avoid instructing emission of the light from the lamp(s) 140 in case the surface is not identified as a treatment area, for example, prevent the trigger button from triggering release of the regulated energized pulse. Optionally, the front-end control unit 134 collects the sensory data from the light sensor of the proximity assembly(s) 138 and transmits it to the control unit 114 which may analyze the sensory data to allow release of the regulated energized pulse according to the identified surface.

Optionally, the treatment unit 104 includes one or more imaging sensor 144, for example, a camera, an infrared camera, a thermal sensor and/or the like adapted to depict the treatment area and capture one or more images of the treatment area.

The control unit 114 may analyze the image(s) captured by the imaging sensor(s) 144 and/or the sensory data captured by the light sensor of the proximity assembly(s) 138 to identify one or more treatment area characteristics, for example, a skin color, a hair color, a hair type and/or the like. The imaging sensor(s) 144 may be deployed, located, positioned and/or adapted to depict the treatment area when the treatment face 142 is placed on the treatment area and/or the treatment face is in close proximity to the treatment area.

The control unit 114 may employ one or more image processing methods, tools and/or algorithms to analyze the image(s) captured by the imaging sensor(s) 144 in order to identify the treatment area characteristic(s). The control unit 114 may operate the PFN 116 to construct the regulated energized pulse according to the identified treatment area characteristics. For example, assuming the treatment area is determined to be a dark skin, the control unit 114 may operate the PFN 116 to generate the regulated energized pulse having significantly long pulses since the dark skin may be less susceptible to the induced heat and the increased heat may be more effective for the IPL session. In another example, assuming the treatment area is determined to be a light skin, the control unit 114 may operate the PFN 116 to generate the regulated energized pulse having short pulses to avoid damaging, burning and/or hurting the treatment area since the light skin may be highly sensitive to excessive heat. In another example, assuming the hair at the treatment area is determined to be thick hair, the control unit 114 may operate the PFN 116 to generate the regulated energized pulse having longer pulses to effectively destroy the thick hair (root) cells which may be significantly durable to the induced heat.

The control unit 114 may apply one or more algorithms to operate the PFN 116 in order to generate the regulated energized pulses with desired multi-level voltage waveform patterns defined for causing the lamp(s) 140 to emit sequences of light pulses inducing heat to the treatment area at temperature levels and/or patterns optimal for one or more of the IPL treatments. The lamp(s) 140 may emit light pulses proportional to the voltage and/or current levels of the regulated energized pulse since one or more light emission attributes of the light pulses emitted by the lamp(s) 140, for example, shape, level, intensity, spectrum, distribution and/or the like may be direct function of the current and/or voltage of the regulated energized pulses.

In order to generate the regulated energized pulses, the control unit 114 may operate the PFN 116, specifically, one or more of the switches 212, one or more of the electrical regulators 214 and/or the like in order to adjust the pattern of the desired multi-level voltage waveform which may be optimal for the IPL treatment. The control unit 114 may thus adjust one or more parameters of the multi-level voltage waveform to set the desired pattern for the regulated energized pulse, for example, a number of pulses, a power of each of the pulses, a level of the high voltage level and/or of the low voltage level of each pulse, a duration of the high voltage level and/or of the low voltage level segment of each pulse, a high and/or low current level of each pulse and/or the like. For example, the control unit 114 may apply one or more Pulse-width modulation (PWM) elements which may control the state (open/close) of the switches 212 and/or to control one or more operational parameters of the electrical regulators 214, for example, a duty cycle, an OFF time period, an ON time period, a switching frequency and/or the like. The control unit 114 may further configure, operate and/or instruct the power supply 110 to adjust the input feed to the capacitor units 210 according to the output voltage level(s) of the desired multi-level voltage waveform.

Figure 3A:
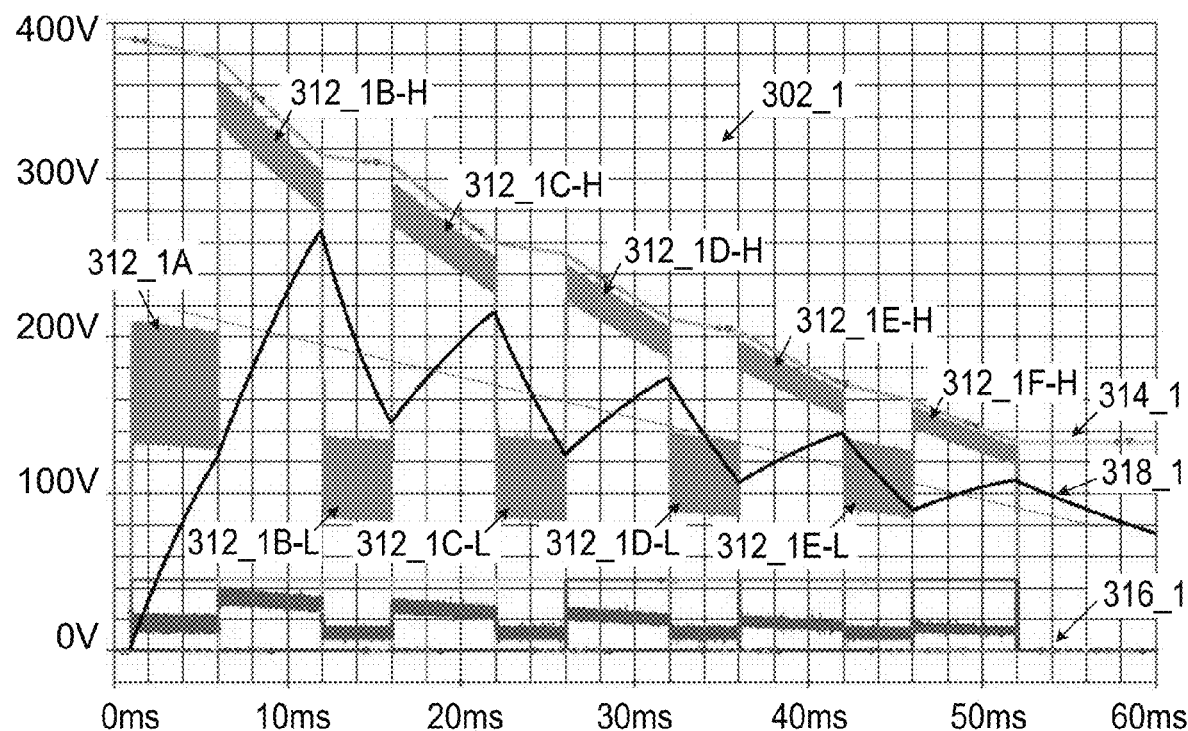
Figure 3B:
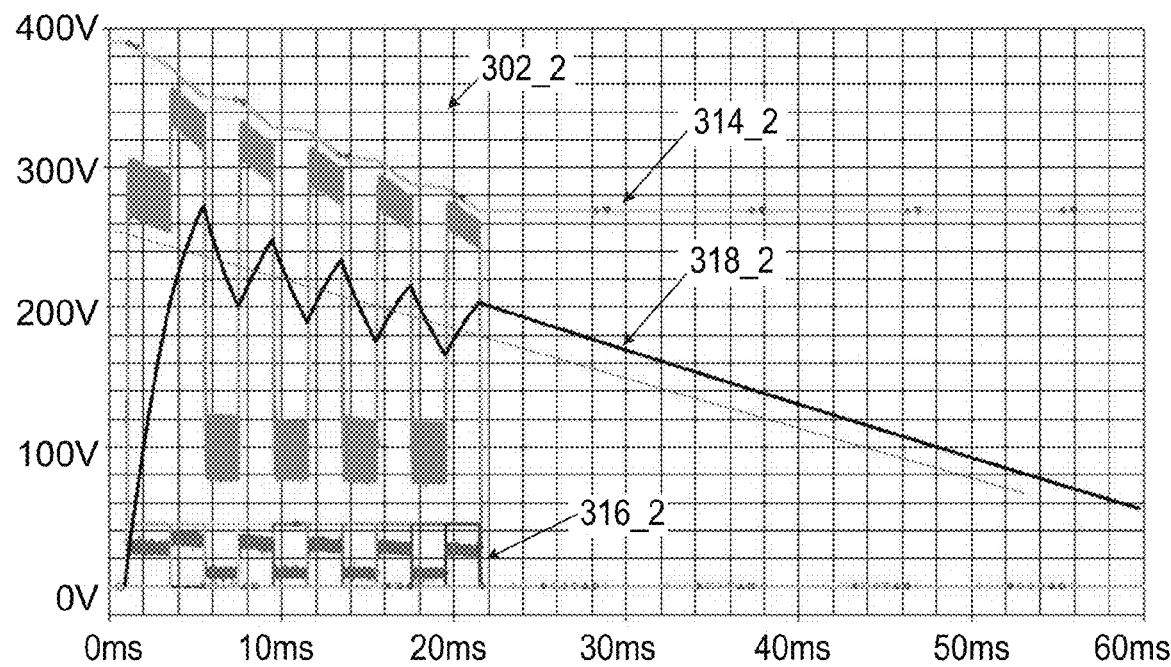
Figure 3C:
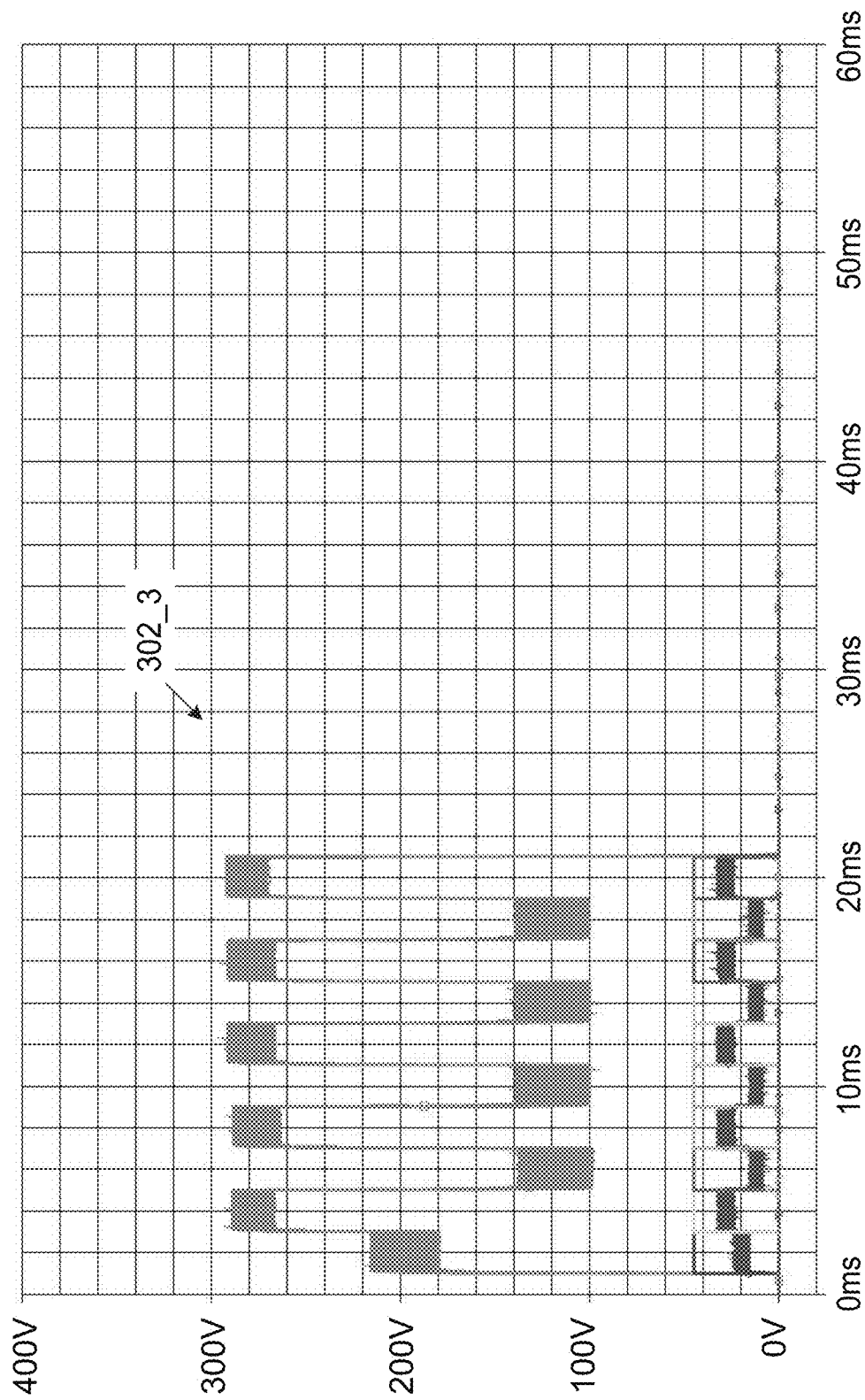

Reference is now made to FIG. 3A, 3B and FIG. 3C, which are graph charts of exemplary regulated energized pulses having desired multi-level voltage waveform patterns adapted to drive an IPL lamp of an IPL apparatus, according to some embodiments of the present invention. FIG. 3A presents a graph chart of an exemplary regulated energized pulse 302_1 which may be generated by a PFN such as the PFN 116 operated by a main controller such as the control unit 114 executed by a control unit such as the control unit 114 and driven to a lamp such as the lamp 140.

The regulated energized pulse 302_1 (marked green) has a multi-level voltage waveform pattern comprising a sequence of five pulses 312_1 (i.e. 312_1B, 312_1C, 312_1D, 312_1E and 312_1F) spread over a time period of about 50 ms (milliseconds). The pulses 312_1 may be generated by modules such as the modules 202 of the PFN 116 which discharge the energy stored in their respective capacitor units such as the capacitor units 210 and regulate the energy through electrical regulators such as the electrical regulators 214. For example, each of the pulses 312_1 may be generated by a respective one of the modules 202 which discharges the energy stored in its respective capacitor unit 210 regulated by the respective electrical regulator 214.

The voltage level of the regulated energized pulse 302_1, designated 314_1, expresses the voltage level of the energy discharged by capacitor units 210 and regulated by the electrical regulators 214. The current level of the regulated energized pulse 302_1, designated 316_1, expresses the current level of the energy discharged by capacitor units 210 and regulated by the electrical regulators 214. The regulated energized pulse 302_1 is driven to the lamp 140 which may emit the light pulses according to the waveform of the regulated energized pulse 302_1. The light pulses may induce heat to the treatment area in a heat profiler (pattern) that follows the waveform of the regulated energized pulse 302_1. The heat level induced by the light pulses is designated 318_1.

As shown, each of the pulses has a high voltage level segment 312_1xH and a low voltage level segment 312_1xL, for example, a pulse 312_1B has a high voltage level segment 312-1B-H and a low voltage level segment 312_1B-L, a pulse 312_1C has a high voltage level segment 312_1C-H and a low voltage level v312_1C-L, a pulse segment 312_1D has a high voltage level segment 312_1D-H and a low voltage level segment 312_1D-L and a pulse segment 312_1E has a high voltage level segment 312_1E-H and a low voltage level segment 312_1E-L. A final pulse 312_1F may only have a high voltage level segment 312_1F-H before the PFN is operated to stop driving the regulated energized pulse 302_1.

The control unit 114 may operate the PFN 116 to adjust the pattern of the multi-level voltage waveform of the regulated energized pulse 302_1 in order to create the desired multi-level voltage waveform to create the heat profile optimal for the IPL treatment. The control unit 114 may adjust one or more parameters of the multi-level voltage waveform to set the desired pattern, for example, a number of the pulses 312_1, a level of the high voltage level segment 312_1xH and/or of the low voltage level segment 312_1xL, a duration of the high voltage level segment 312_1xH and/or of the low voltage level segment 312_1xL, a high and/or low current level of the pulses 312_1 and/or the like.

The lamp 140 may have a minimal heating voltage which is required to excite the lamp 140 to start emitting light. Exciting the lamp 140 into its operational state may be time consuming and the heating (exciting) time may be a relatively long, for example, 6 ms-8 ms. However, by maintain a non-zero significantly low voltage driven to the lamp 140, the lamps may be maintained in operation thus avoiding the need to excite them again into the operational state and avoiding the exciting time.

As seen for the regulated energized pulse 302_1, the high voltage level segments 312_1xH may reach high voltage levels, for example, in the range of 80V-400V. The lamp 140 may therefore emit high intensity light during the high voltage level segment 312_1xH periods and induce a significantly high heat level to the treatment area. The high voltage level segments 312_1xH may gradually decrease for each succeeding pulse 312_1 in order to avoid excessive heating of the treatment area. The voltage levels may naturally be adjusted by the control unit 114 according to the light emission attributes of the lamp 140. The low voltage level segments 312_1xL are defined to be significantly above the lamp heating voltage and may be in a range of 20%-40% of the maximum high voltage level of the regulated energized pulse 302_1, i.e. of the high voltage level segment 312_1B-H. For example, the low voltage level segments 312_1xL may be set to a voltage of 80V-160V. As the low voltage level segments 312_1xL are set to a voltage which is above the heating voltage threshold the lamp 140 is constantly in operational (active) state and there is no need to excite the lamp 140 into operation at the beginning of each pulse 312_1.

As seen in the graph, the heat profile as expressed by heat level 318_1 maintains a significantly high bias which is maintained through the significantly high low level voltage segment 312_1xL. However, as the regulated energized pulse 302_1 is highly dynamic, during the highly dynamic high voltage level segment 312_1B-H, the heat level may rapidly vary between the bias level and extremely high heat levels thus inducing extreme heat changes to the treatment area.

By setting the low voltage level segments 312_1xL to the 20%-40% of the maximum high voltage level segment 312_1B-H, the lamp 140 may emit sufficient light to maintain a significantly high heat level to the treatment area while avoiding extreme heat exposure to the treatment area for prolonged time thus significantly reducing probability of damage, destruction, burn and/or the like to the treatment area. Moreover, by maintaining the low voltage level segments 312_1xL at 20%-40% of the maximum high voltage level, the heat level induced over the treatment area may be significantly stable thus avoiding extreme variations in the heat level applied to the treatment area. This may further reduce the probability of damage, destruction, burn and/or the like to the treatment area.

Moreover, by maintaining the low voltage level segments 312_1xL at significantly high levels may prevent cooling of the treatment area between the high voltage level segments 312_1xH. This may significantly reduce the energy required to heat the treatment area again during the succeeding pulse 312_1. The high voltage level segments 312_1xH may therefore be significantly reduced thus requiring lower capacity capacitor units 210 and/or reducing the stress applied to the capacitor units 210. As such, the capacitor units 210 may be lower capacity and hence lower cost devices significantly reducing the cost of the PFN 216. In addition, as the stress on the capacitor units 210 may be reduced, the capacitor units 210 may have improved longevity, improved endurance and/or the like.

Furthermore, the high voltage level segments 312_1xH may require significantly low current and/or voltage regulation while the low voltage level segments 312_1xL may require little and typically no current and/or voltage regulation at all. This may allow using simple and/or low end electrical regulators 214 thus significantly reducing the cost of the PFN 216.

Optionally, the control unit 114 main controller 170 operates the PFN 116 to construct the regulated energized pulse 302_1 to include a first lamp pre-heating pulse 312_1A preceding the operational pulses 312_1B through 312_1F. The control unit 114 main controller 170 may operate the PFN 116 to create the lamp pre-heating pulse 312_1A with a voltage level in the range of 40%-75% of the maximum high voltage level of the regulated energized pulse 302_1, i.e. of the high voltage level segment 312_1B-H. The lamp pre-heating pulse 312_1A may excite the lamp 140 into operation. Moreover, by setting the voltage level of the lamp pre-heating pulse 312_1A to a relatively low voltage level, for example, 40% of the maximum high voltage level, the heat induced by the lamp 140 in response to driving the lamp pre-heating pulse 312_1A may be moderate. This may be done to avoid inflicting a thermal shock to the treatment area as may happen in case the high voltage level segment 312_1B-H is first driven to the lamp 140 which in response may induce extremely high heat level over the treatment area.

FIG. 3B presents a graph chart of an exemplary regulated energized pulse 302_2 which may be generated the PFN 116 operated by the control unit 114 and driven to the lamp 140. The regulated energized pulse 302_2 (marked green) exhibits the same basic pattern as the regulated energized pulse 302_1 with some parameters modifications thus producing a different pattern for the regulated energized pulse 302_2. Specifically, the duration of the high voltage level segments and of the low voltage segments is reduced compared to those of the regulated energized pulse 302_1 thus resulting in a shorter duration regulated energized pulse 302_2. While the regulated energized pulse 302_1 may be highly efficient for some IPL treatments, specifically, hair removal for dark skin patients, the regulated energized pulse 302_2 may be efficient for hair removal for light and/or pale skin patients. This is since light and/or pale skin may be highly susceptible to extreme heat and it may therefore be desirable to avoid exposure of such skin to high heat for prolonged time periods. As described for the regulated energized pulse 302_1, the control unit 114 may operate the PFN 116 to construct the regulated energized pulse 302_1 with a pre-heating pulse which may be set, for example, to 75% of the maximum high voltage level. The heat induced by the lamp 140 in response to driving the lamp pre-heating pulse may be significantly high thus heating the treatment area to a desired level before applying the succeeding pulses. This may allow raising the temperature of the treatment area to a significantly high heat level which may be an optimal starting point for the IPL session while avoiding a major thermal shock to the treatment area.

In some embodiments of the present invention, the control unit 114 may operate the PFN 116 to construct the regulated energized pulse with the high voltage level segment having an equal duration and/or voltage level and the low voltage level segment having an equal duration and/or voltage level.

FIG. 3C presents a graph chart of an exemplary regulated energized pulse 302_3 which may be generated the PFN 116 controlled by the control unit 114 executed by the control unit 114 and driven to the lamp 140. The waveform pattern of the regulated energized pulse 302_3 (marked green) may exhibit some similarity to the pattern of the regulated energized pulse 302_2 specifically with respect to the timing, i.e. duration (width) of the pulse segments. However, the regulated energized pulse 302_3 may be constructed to have its high voltage level segments share an equal duration and equal voltage level and also its low voltage level segments are constructed with an equal duration and equal voltage level. The equal segments of the regulated energized pulse 302_3 may be optimal for one or more of the IPL treatments since the equal duration and equal voltage levels may allow achieving maximal variation (difference) of the level of heat induced on the treatment area.

Figure 4:
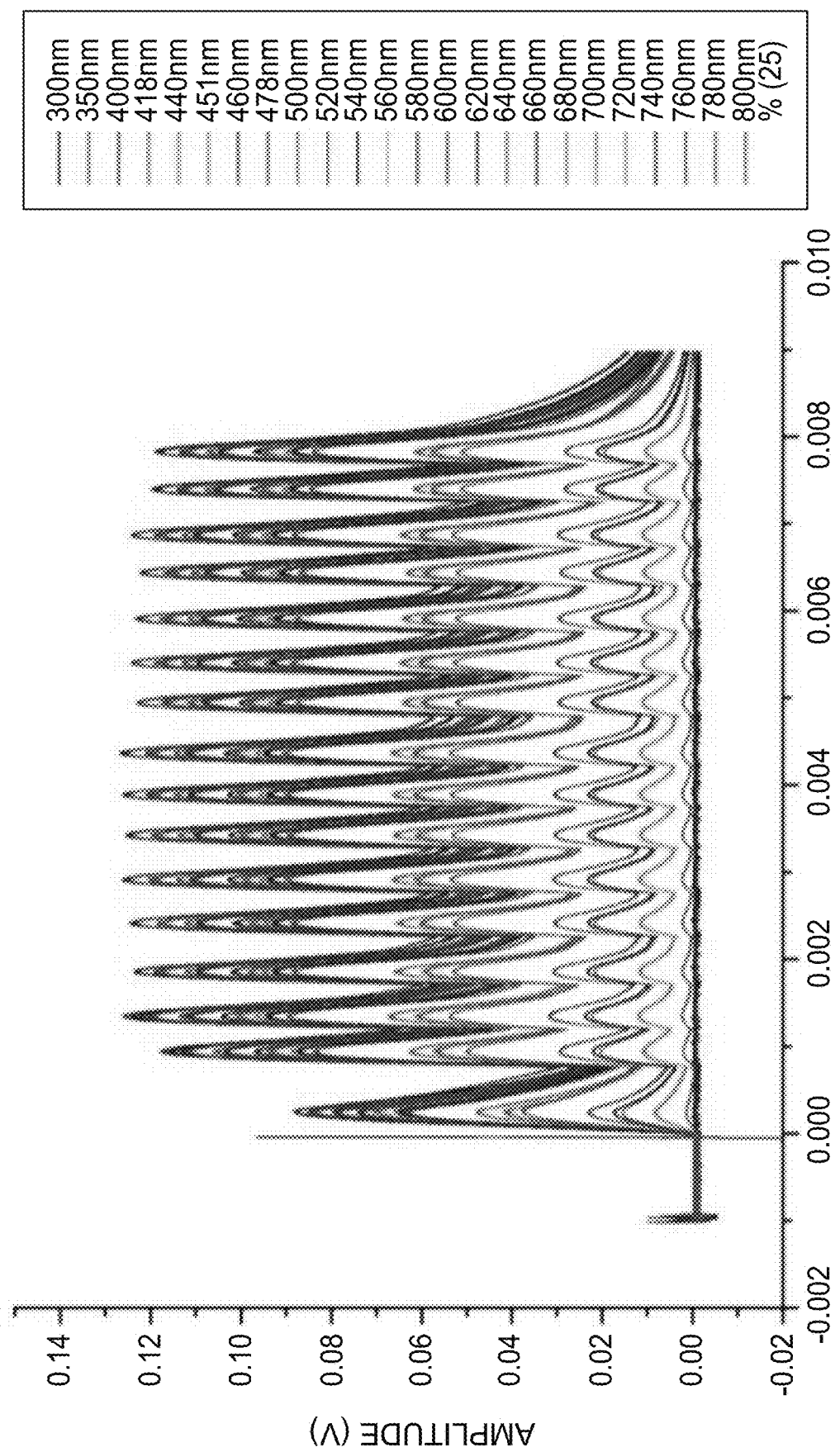

Reference is now made to FIG. 4, which is a capture of a spectrometer image of a light emission spectrum generated by an IPL lamp driven with an exemplary regulated energized pulse having a desired multi-level voltage waveform pattern, according to some embodiments of the present invention. FIG. 4 presents a spectrum as measured by a spectrometer used for measuring the spectrum of light emission of an exemplary IPL lamp such as the lamp 140 fed with an exemplary regulated energized pulse to induce heat to the treatment area. The simulation presents some of the light emission attributes of the light pulses emitted by the lamp 140 to induce heat along the time axis, specifically, the shape, the level, the intensity and the spectrum. Each of the light pulses may generate heat and the overall heat applied to the treatment area is the sum of the heat induced by each of the light pulses. Since the light pulses are emitted by the lamp(s) 140 proportionally to the regulated energized pulse, a main controller such as the control unit 114 may operate a PFN such as the PFN 116 to generate the regulated energized pulse to excite the lamp(s) 140 to emit the light pulses at a desired pattern with one or more desired emission attributes, for example, intensity, spectrum and/or the like. The pattern as well as the emission attributes of the light pulses may be adjusted by the control unit 114 according to one or more characteristics of the treatment area of the patient.

Figure 5A:
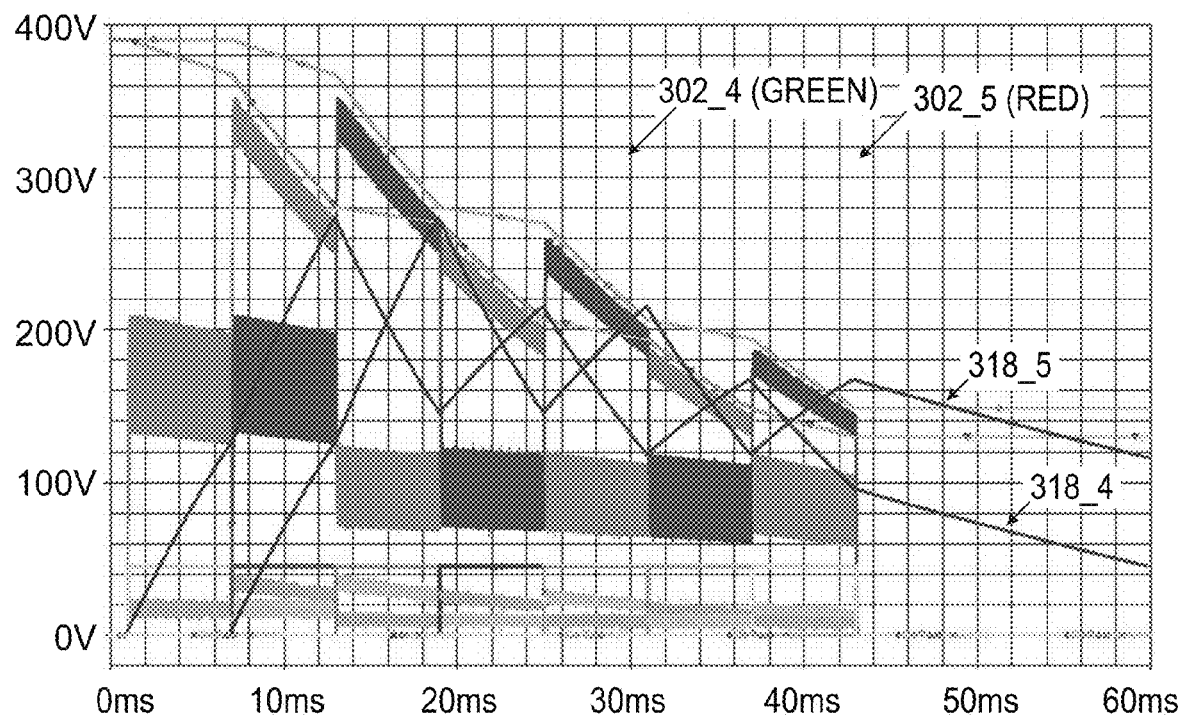
Figure 5B:
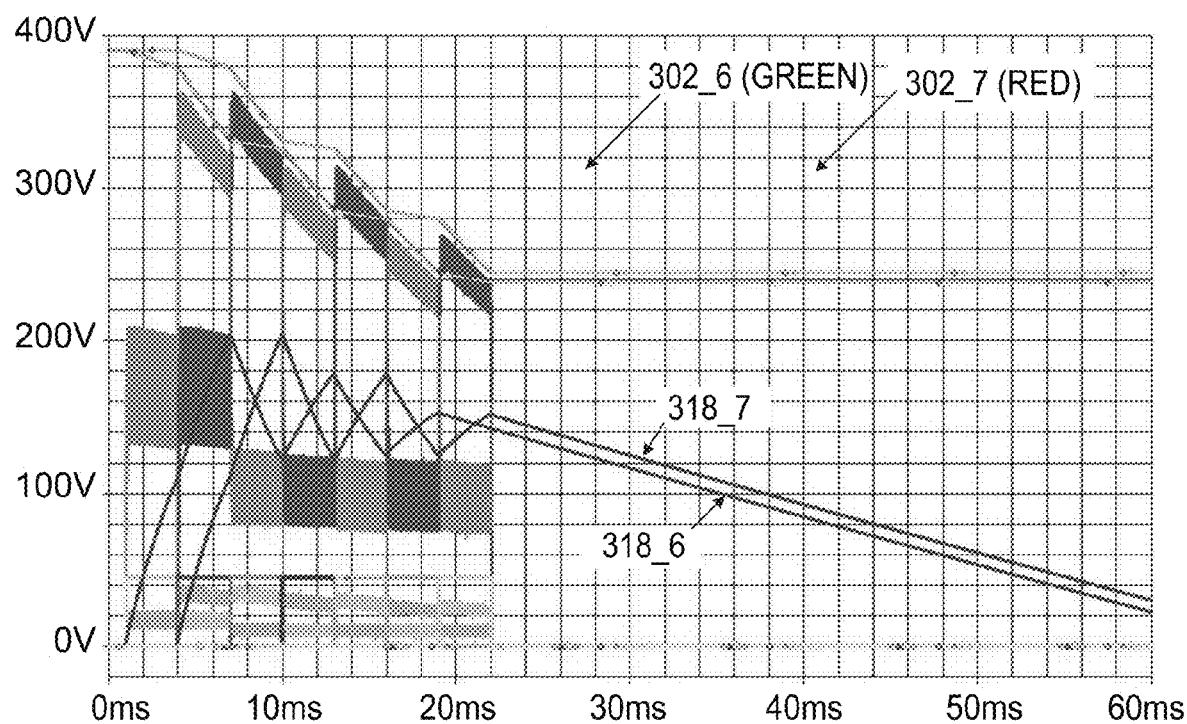

Reference is now made to FIG. 5A and FIG. 5B, which are graph charts of exemplary pairs of regulated energized pulses having desired multi-level voltage waveform patterns adapted to drive a pair of IPL lamp of an IPL apparatus, according to some embodiments of the present invention. FIG. 5A presents a graph chart of two exemplary regulated energized pulses 302_4 (marked green) and 302_5 (marked red) which may be generated by a PFN such as the PFN 116 operated by a control unit such as the control unit 114 and driven to two lamps such as the lamp 140. The two lamps 140 may be designed, located, positioned and/or adapted to cover a larger treatment area. Moreover, the control unit 114 may operate the PFN 116 to generate the regulated energized pulses 302_4 and 302_5 with alternating multi-voltage waveform patterns such that while the first lamp 140 is fed with high level pulse segments such as the high level pulse segments 312_1$x$H, the second lamp 140 is fed with low level pulse segments such as the low level pulse segments 312_1$x$L. In such implementation the illumination intensity of the light pulses emitted by the two lamps 140 alternates to produce a significant heat level 318_4 and 318_5 respectively over the treatment area. The heat induced by the combined light pulses emitted by the two lamps 140 may reduce the energy required for feeding each of the lamps 140 and hence reduce the energy required from the PFN 116. As such, the PFN 116 may utilize lower capacity and hence lower cost capacitor units such as the capacitor units 210 thus further reducing the cost of the PFN 116. In addition, as the stress on the capacitor units 210 may be reduced, the capacitor units 210 may have improved longevity, improved endurance and/or the like. Moreover, reducing the dynamic heat pulse may prevent excessive thermal shocks to the treatment area thus reducing probability of undesired damage to the cells of the treatment area.

As described for the single lamp 140, the control unit 102 may operate the PFN 116 to construct each of the regulated energized pulses 302_4 and 302_5 to include a respective pre-heating pulse. As discussed before, this may serve to prevent the thermal shock to the treatment area and/or to the lamps 140.

FIG. 5B presents a graph chart of two exemplary regulated energized pulses 302_6 (marked green) and 302_7 (marked red) which may be generated the PFN 116 operated by the control unit 114 and driven to the two lamps 140. The regulated energized pulses 302_6 and 302_7 exhibit the same basic pattern as the regulated energized pulses 302_4 and 302_5 respectively with some parameters modifications thus producing a different pattern for the regulated energized pulses 302_6 and 302_7. Specifically, the duration of the high voltage level segments and of the low voltage level segments is reduced compared to those of the regulated energized pulse 302_4 and 302_5 thus resulting in shorter duration regulated energized pulses 302_6 and 302_7 and hence reduced heat levels 318_6 and 318_7 respectively. As described before, the overall duration of the regulated energized pulses 302_4, 302_5, 302_6 and 302_7 may be adjusted according to the characteristics of the treatment area, specifically according to the skin of the patient.

The control unit 102 may operate the PFN 116 to construct each of the regulated energized pulses 302_6 and 302_7 to include a respective pre-heating pulse. As discussed before, this may serve to prevent the thermal shock to the treatment area and/or to the lamps 140.

Figure 5C:
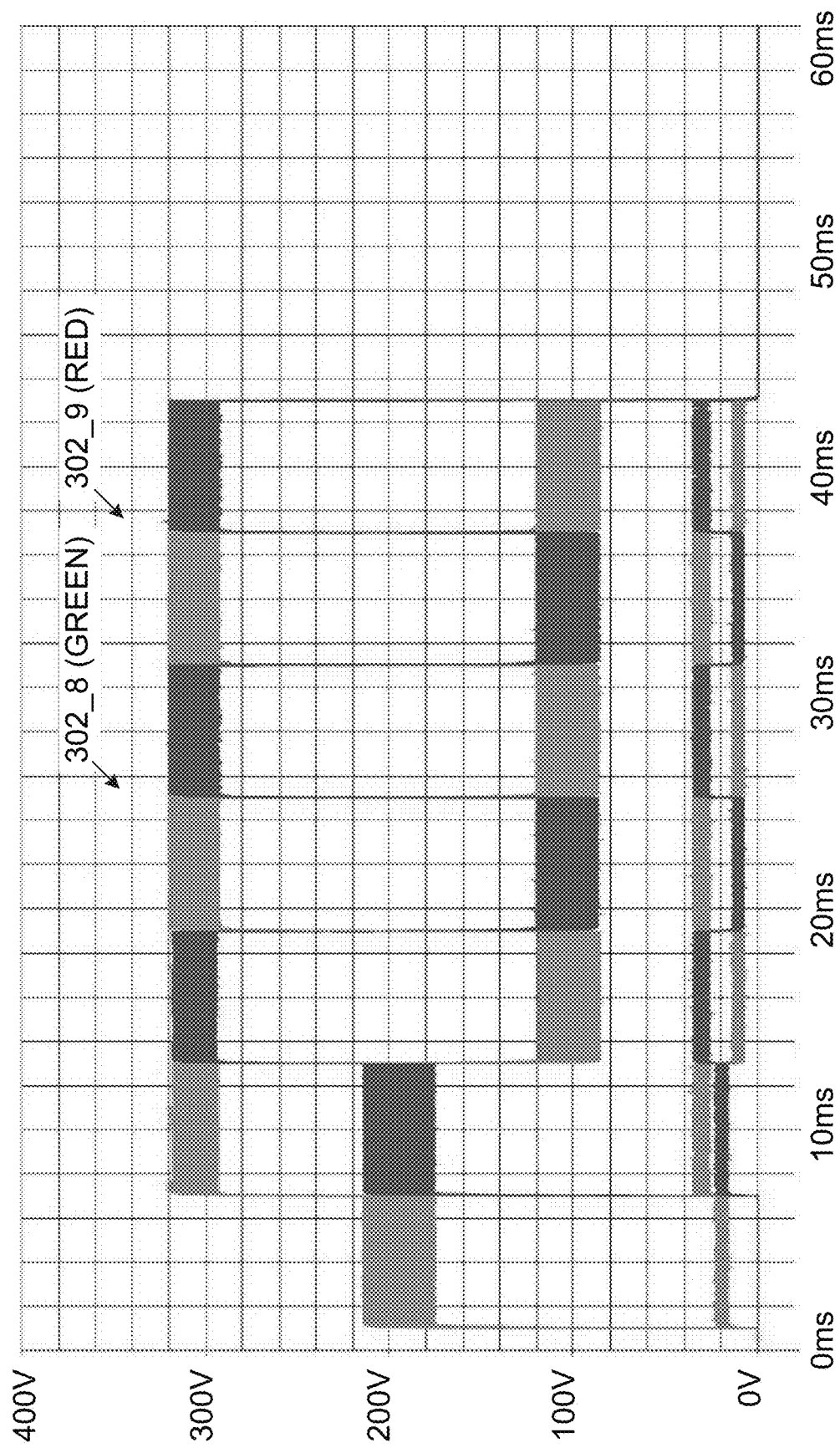

FIG. 5C presents a graph chart of two exemplary regulated energized pulses 302_8 (marked green) and 302_9 (marked red) which may be generated the PFN 116 operated by the control unit 114 and driven to the two lamps 140. The waveform pattern of the regulated energized pulses 302_8 and 302_9 may exhibit some similarity to the pattern of the regulated energized pulses 302_4 and 302_5 respectively, specifically with respect to the timing, i.e. duration (width) of the pulses segments. However, the regulated energized pulses 302_8 and 302_9 may be constructed to have their high voltage level segments share an equal duration and an equal voltage level. Similarly, the low voltage level segments of the regulated energized pulses 302_8 and 302_9 are constructed with an equal duration and equal voltage level. The equal segments of the regulated energized pulses 302_8 and 302_9 may be optimal for one or more of the IPL treatments since the equal duration and equal voltage levels may allow achieving maximal variation (difference) of the level of heat induced on the treatment area.

The control unit 102 may operate the PFN 116 to construct each of the regulated energized pulses 302_8 and 302_9 to include a respective pre-heating pulse. As discussed before, this may serve to prevent the thermal shock to the treatment area and/or to the lamps 140.

Figure 6A:
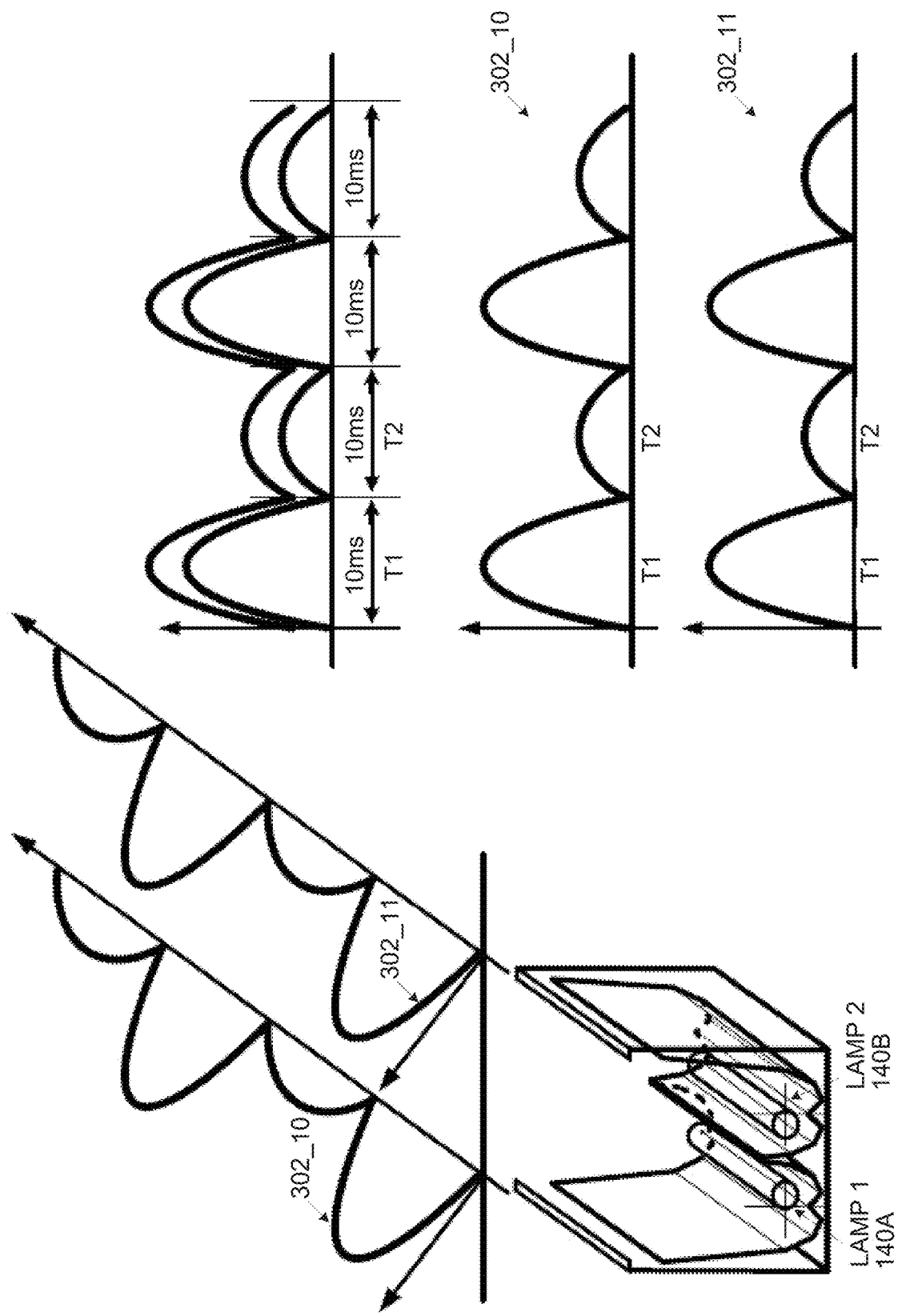
Figure 6B:
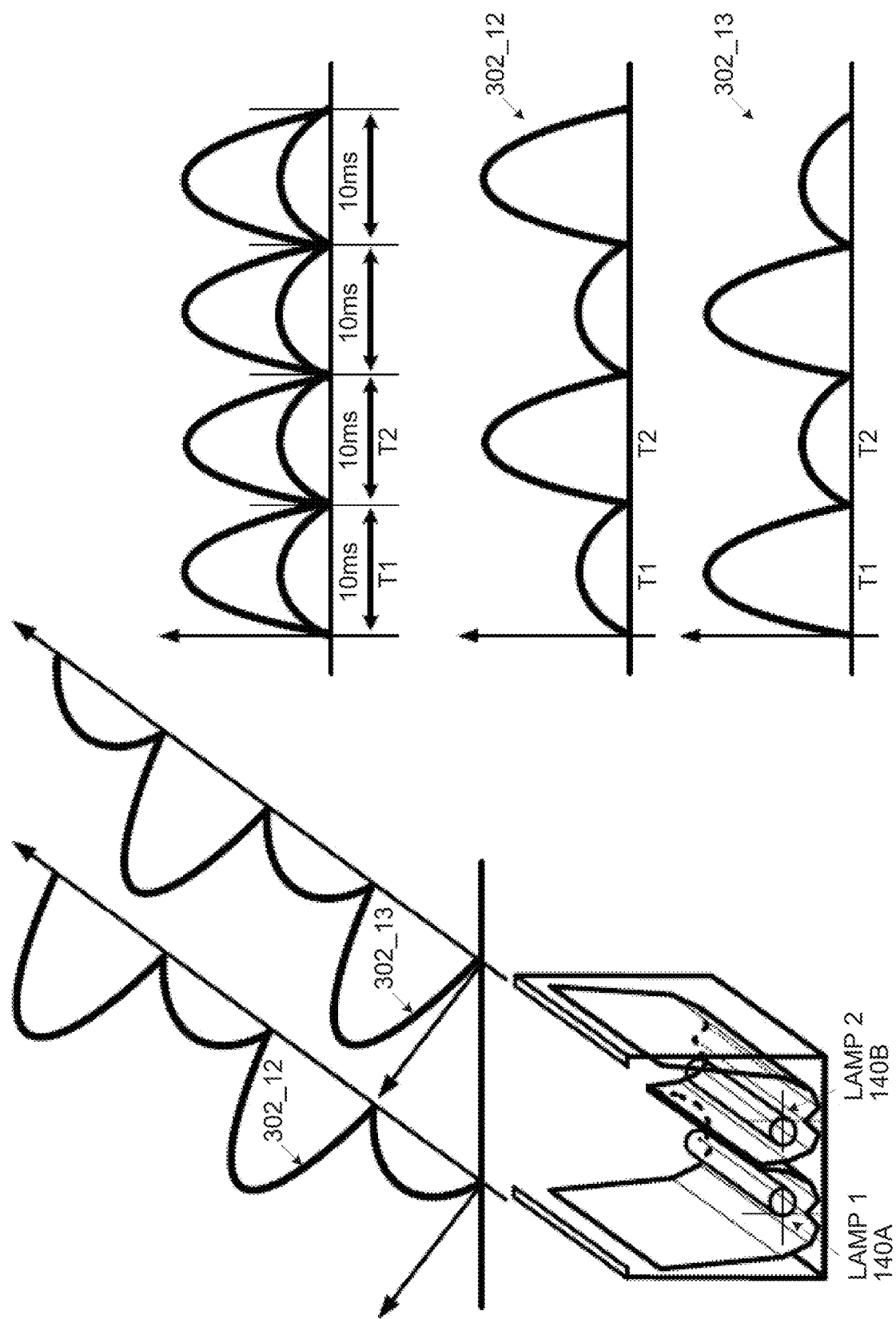

Reference is now made to FIG. 6A and FIG. 6B, which are schematic illustrations of exemplary pairs of regulated energized pulses having synchronized and alternating multi-level voltage waveform patterns adapted to drive a pair of IPL lamp of an IPL apparatus, according to some embodiments of the present invention.

FIG. 6A is a schematic illustration presenting a pair of lamps 140A and 140B such as the lamp 140 fed with two synchronized exemplary regulated energized pulses 302_10 and 302_11 respectively which may be generated by a PFN such as the PFN 116 operated by a control unit such as the control unit 114. As shown, the regulated energized pulses 302_10 and 302_11 are synchronized such that high level pulse segments such as the high level pulse segments 312_1$x$H of the two regulated energized pulses 302_10 and 302_11 occur at the same time. Similarly, low level pulse segments such as the low level pulse segments 312_1$x$L of the two energized pulses 302_10 and 302_11 are also adjusted to occur at the same time. For any given time instance, the illumination of the light pulses emitted by the lamps 140A and 140B is accumulated (summed) thus reflect the combination of the light pulses emitted by the lamps 140A and 140B. The combination of the light pulses may be a function of the combination of the regulated energized pulses 302_10 and 302_11 driven to the lamps 140A and 140B. Driving the synchronized regulated energized pulses 302_10 and 302_11 to the respective lamps 140A and 140B may induce extremely dynamic heat levels, i.e. induce large variations between the low temperatures and high temperatures on the treatment area. Such highly dynamic heat may be highly effective for treating certain types of skin, hair and/or the like, for example, dark skin, thick hair and/or the like. Additionally and/or alternatively, assuming the lamps 140A and 140B are located, positioned and/or adapted to distribute their light pulses over the same treatment area, in order to achieve the same heat level (temperature) as a single lamp 140, the regulated energized pulses 302_10 and 302_11 feeding the two lamps 140A and 140B may have significantly less energy than the regulated energized pulse required to feed the single lamp 140. The PFN 116 may therefore utilize lower capacity and hence lower cost capacitor units such as the capacitor units 210 thus reducing the cost of the PFN 116. In addition, as the stress on the capacitor units 210 may be reduced, the capacitor units 210 may have improved longevity, improved endurance and/or the like. Due to the lower stress on the lamps 140A and 140B, their longevity and/or endurance may also be significantly increased.

FIG. 6B is a schematic illustration presenting the pair of lamps 140A and 140B fed with two alternating exemplary regulated energized pulses 302_12 and 302_13 respectively which may be generated by the PFN 116 operated by the control unit 114. As shown, the regulated energized pulses 302_12 and 302_13 are alternating such that the high level pulse segments of the regulated energized pulses 302_12 occur during the time of the low level pulse segments of the regulated energized pulses 302_13. Similarly the low level pulse segments of the regulated energized pulses 302_12 occur during the time of the high level pulse segments of the regulated energized pulses 302_13. For any given time instance, the illumination intensity of the light pulses emitted by the lamps 140A and 140B is accumulated (summed) thus reflect the combination of the light pulses emitted by the lamps 140A and 140B. The combination of the light pulses may be a function of the combination of the regulated energized pulses 302_7 and 302_8 driven to the lamps 140A and 140B. Driving the alternating regulated energized pulses 302_12 and 302_13 to the respective lamps 140A and 140B may reduce the dynamic heat levels, i.e. reduce the variation between the low temperatures and high temperatures induced on the treatment area. Such reduced dynamic heat may be highly effective for sensitive skin, for example, light color skin since excessive thermal shock to the treatment area may be reduced and/or prevented. Additionally and/or alternatively, the lamps 140A and 140B may be located, positioned and/or adapted to distribute their light pulses over different treatment areas thus significantly increasing the treatment area induced with heat during each treatment cycle.

The IPL apparatus 100, in particular, the treatment unit 104 may include one or more reflectors shaped, configured, located and/or positioned to direct the light pulses emitted by the lamp(s) 140 towards the treatment face 142 and hence towards the treatment area to which the treatment face 142 is applied. This may significantly increase the light energy directed to the treatment area. Moreover, the reflector(s) may be shaped, configured, located and/or positioned to increase efficiency of illumination distribution of the light pulses emitted, for example, to improve an even illumination distribution of the light pulses and/or the like. The reflector(s) may be produced of one or more materials having high light reflection characteristics, for example, a metal foil, a ceramic material, a polymeric material and/or the like. By increasing the illumination of the light pulses in the direction of the treatment area, the reflector may significantly improve energy utilization of the light pulses. As such the heat induced by the light pulses may be significantly increased. Additionally and/or alternatively, lower power lamp(s) 140 may be used. Moreover, directing most of the light energy to the treatment area may significantly increase accuracy of the induced heat since the intensity of the directed illumination may be better controlled.

Reference is now made to FIG. 7A, FIG. 7B and FIG. 7C, which are schematic illustrations of exemplary reflectors of exemplary IPL apparatuses having one, two and a plurality of IPL lamps respectively, according to some embodiments of the present invention. FIG. 7A presents an exemplary reflector 702A disposed around a lamp such as the lamp 140 placed in a lamp compartment of an IPL apparatus such as the IPL apparatus 100. The reflector 702A may be shaped, configured, located and/or positioned to reflect light emitted by the lamp 140 towards a treatment face 142. In particular, the reflector 702A may be shaped to have multiple curvatures each having a respective angle defined to reflect the light emitted by the lamp 140 and hitting the respective part of the reflector 702A towards the treatment face 142. By reflecting a significant amount of light pulses energy towards the treatment face 142, the energy of light heating the treatment area as well as the illumination distribution of the light pulses may be significantly increased thus effectively achieving an increased and even heat induction over the entire treatment area. This may significantly improve energy utilization of a PFN such as the PFN 116 operated by a control unit such as the control unit 114 of the IPL apparatus 100.

FIG. 7B presents an exemplary asymmetric reflector 702B disposed around a pair of lamps 140A and 140B placed in one or more lamp compartments of the IPL apparatus 100. The asymmetric reflector 702B may be shaped, configured, located and/or positioned to reflect light emitted by the lamps 140A and 140B towards the treatment face 142. Each of the lamps 140A and 140B may typically be shaped in a cylindrical shape to emit light along a longitudinal axis of the lamps 140A and 140B respectively. The asymmetric reflector 702B may therefore be shaped asymmetrically around each of the lamps 140A and 140B such that along a side of the longitudinal axis of the lamps 140A and 140B which faces the other lamp 140A or 140B, the reflection surface of the asymmetric reflector 702B extends to approximately the height of the lamps 140A and 140B. The asymmetric reflector 702B may be further shaped to have its reflection surface extending significantly high above the lamps 140A and 140B on the side of the longitudinal axis facing away from the other lamp 140A or 140B, i.e. facing a wall of a lamp compartment. For example, at the side of the longitudinal axis of the lamps 140A and 140B facing away from each other, the asymmetric reflector 702B may be shaped with the reflection surface extending to approximately the treatment face 142.

The asymmetric reflector 702B may be shaped to have multiple curvatures each having a respective angle defined to reflect the light emitted by the lamp 140 and hitting the respective part of the asymmetric reflector 702B towards the treatment face 142. The asymmetric reflector 702B may be further shaped to prevent direct line of sight between the two lamps 140A and 140B to prevent mutual illumination which may stress and potentially damage one or more of the lamps 140A and 140B, the lamp compartment and/or the like. It should be noted that the dimensions presented in FIG. 7B are exemplary and should not be construed as limiting. The asymmetric reflector 702B may significantly increase illumination distribution of the light pulses emitted by the lamps 140A and 140B over the treatment face 142 which may therefore be significantly increased to cover a larger treatment area treated during each treatment cycle. Moreover, in case of alternating regulated energized pulses, for example, the regulated energized pulses 302_12 and 302_13, the accumulated illumination of the light pulses emitted by the lamps 140A and 140B may be efficiently distributed over the treatment face 142. The heat induced to the treatment area may therefore be significantly high which may be effective for the IPL treatment while avoiding extreme variations which may inflict discomfort and/or pain to the patient and even damage and/or burn the treatment area and/or part thereof.

As shown in FIG. 7B, the lamps 140A and 140B may be positioned, located and/or deployed off center of their respective reflection curvatures of the asymmetric reflector 702B. Specifically, the lamps 140A and 140B may be deployed off center their respective reflection surfaces to the side facing the other lamp 140A or 140B. For example, the lamp 140A may be deployed off center its respective reflection surface towards the lamp 140B and the lamp 140B may be deployed off center its respective reflection surface towards the lamp 140A. This may significantly improve direction and/or distribution of the light pulses energy towards the treatment face 142.

FIG. 7C presents an exemplary asymmetric reflector 702C disposed around a plurality of lamps 140A through 140N placed in one or more lamp compartments of the IPL apparatus 100. The asymmetric reflector 702C is an extension of the asymmetric reflector 702B and may be shaped, configured, located and/or positioned to reflect light emitted by the lamps 140A, 140B through 140N towards the treatment face 142. The asymmetric reflector 702C may be shaped asymmetrically around each of the lamps 140A through 140N such that along the side of the longitudinal axis of the lamps 140A through 140N which faces any of the other lamps 140A through 140N, the reflection surface of the asymmetric reflector 702C extends to approximately the height of the lamps 140A through 140N. For the exterior lamps 140A and 140N, the asymmetric reflector 702C may be shaped to have its reflection surface extending significantly high above the lamps 140A through 140N on the side of the longitudinal axis facing away from any of the other lamps 140B and 140N-1 respectively, i.e. facing a wall of a lamp compartment.

As shown in FIG. 7C, the exterior lamps 140A and 140N may be positioned, located and/or deployed off center of their respective reflection curvatures of the asymmetric reflector 702C. Specifically, the lamps 140A and 140N may be deployed off center their respective reflection surfaces to the side facing away from the lamp compartment. This may significantly improve direction of the light energy towards the treatment face 142.

Figure 8A:
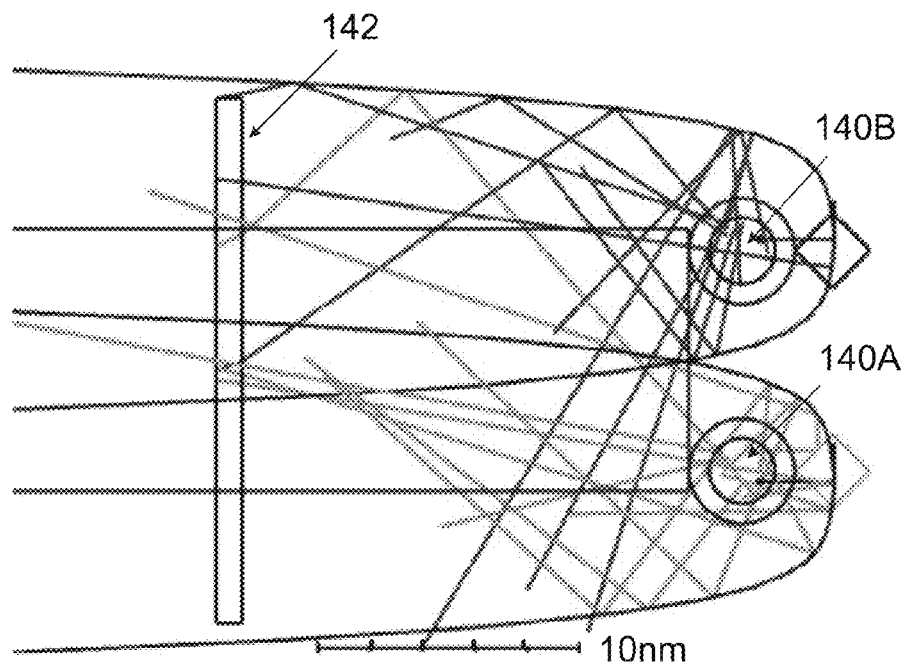
Figure 8B:
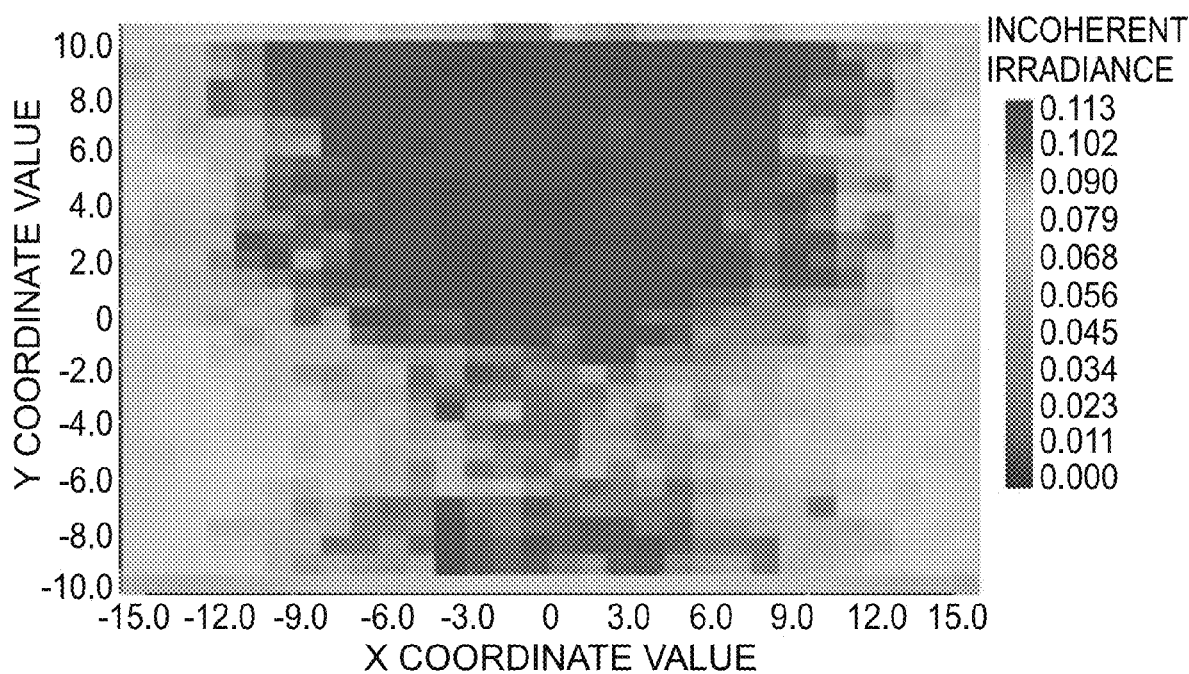

Reference is now made to FIG. 8A, which is a schematic illustration of a simulation of illumination distribution of light emitted by a pair of IPL lamps of an exemplary IPL apparatus having reflectors adapted to reflect the emitted light, according to some embodiments of the present invention. Reference is also made to FIG. 8B, which is a graph chart of a simulation of heat distribution of heat induced by light emitted by two IPL lamps of an exemplary IPL apparatus having reflectors adapted to reflect the emitted light, according to some embodiments of the present invention. FIG. 8A presents a light distribution simulation for light emitted by two lamps such as the lamps 140A and 140B supported by a reflector such as the reflector 702B. As evident from the simulation, the majority of the light emitted by the lamps 140A and 140B is reflected towards a treatment face such as the treatment face 142. FIG. 8B presents a heat map simulation of the heat over the treatment face 142 induced by light pulses emitted by the lamps 140A and 140B supported by the reflector 702B as presented in FIG. 8A. Specifically, the lamps 140A and 140B may be fed with alternating regulated energized pulses, for example, the regulated energized pulses 302_12 and 302_13. Fed (driven) with the alternating regulated energized pulses 302_12 and 302_13, one of the lamps, for example, the lamp 140A may induce a high heat level during the time it is driven with the high voltage pulse segment while the other lamp, for example, the lamp 140B may induce a lower heat level during the time it is driven with the low voltage pulse segment. Therefore, as evident from the heat map in which temperature levels are directly proportional to the color, which presents an instance of time, the upper part of the treatment face 142 is significantly hotter than the lower part of the treatment face 142. However, both the upper part and the lower part are maintained at significantly high temperature which may be effective for the IPL treatment. As such, highly extreme variations in the heat may be avoided thus preventing discomfort and/or pain to the patient as well as preventing damage to the treatment area.

Reference is now made to FIG. 9A, which is a schematic illustration of a treatment unit of an exemplary IPL apparatus utilizing a PFN, according to some embodiments of the present invention. An exemplary treatment unit 104A such as the treatment unit 104 of an IPL apparatus such as the IPL apparatus 100 may be a mobile unit which may be held, grasped, gripped and/or the like by a user such as the user 160 who may maneuver the treatment unit 104A to one or more treatment areas at the patient's body. The treatment unit 104A may be ergonomically modeled and/or shaped for easy and comfortable grip of the user. The treatment unit 104A connects to a base unit such as the base unit 102 through a cable comprising a primary wired interface such as the primary wired interface 150 and optionally an auxiliary wired interface such as the auxiliary wired interface 152.

A treatment side of the treatment unit 104A may include a treatment face such as the treatment face 142 locate above one or more lamp compartments 910 storing one or more lamps such as the lamp 140. The lamp(s) 140 may optionally be hosted in one or more disposable cartridges which may be inserted into the lamp compartment(s) 910. A transparent surface 902 (window treatment) may cover the lamp(s) 140 to prevent direct contact with the lamp(s) 140. The transparent surface 902 may optionally be integrated with the cartridge(s) of the lamp(s) 140. The transparent surface 902 may further include a filter which may filter at least part of the spectrum of light emitted by the lamp(s) 140, specifically light wavelengths which may inflict damage to human skin, i.e. to the treatment area(s). For example, the light pulses emitted by the lamp(s) 140 are generally in the spectral range of 400 to 1200 nm. The filter may selectively filter out lower wavelengths, especially potentially damaging UV light.

The treatment unit 104A may optionally include one or more perimeter illumination light sources 914 for illuminating the treatment area to assist the user 160 and provide him clear visibility of the treatment area during the IPL treatment session. The perimeter illumination light source(s) 914 may be typically disposed, located and/or positioned around a perimeter of the treatment face 142 to effectively illuminate the treatment area.

The treatment face 142 may be at least partially enclosed by a sharpened perimeter edge 904 disposed around at least part of the treatment face 142. The sharpened perimeter edge 904 may be raised above the treatment face 142 such that while applying the treatment face 142 to the treatment area, the sharpened perimeter edge 904 may apply pressure around the treatment area to mark the edges of the treatment area treated during a current IPL session cycle. The markings around the treatment area(s) may allow the user 160 to identify the areas which were treated during previous cycles of the IPL session and efficiently place the treatment face 142 over the treatment area during the current cycle.

In some embodiments of the present invention, the treatment face 142 may be at least partially enclosed by a color applying perimeter edge 912 disposed around at least part of the treatment face 142. The color applying perimeter edge is optionally raised above the treatment face 142. When placing the treatment face 142 over the treatment area, the color applying perimeter edge 912 may apply color, for example, a UV ink and/or the like to the treatment area's edges thus marking the treatment area treated during a current IPL session cycle. This may also allow the user 160 to identify the areas which were treated during previous cycles of the IPL session and efficiently place the treatment face 142 over the treatment area during the current cycle. The color applying perimeter edge 912 may further color one or more guide markings, for example, an alignment line and/or the like. During a current IPL session cycle, the user 160 may align the treatment face 142 with the alignment line(s) which mark one or more treatment areas treated during previous cycles of the IPL session. The treatment unit 104A may further include one or more light sources 906, for example, a UV lamp, a UV LED and/or the like to illuminate the treatment area and make the UV ink markings (applied by the color applying perimeter edge 912) visible to the user 160. The light sources 906 may be located around the perimeter of the treatment face 142 to effectively illuminate the UV ink markings applied by the color applying perimeter edge 912 on the treatment area(s).

Reference is now made to FIG. 9B, which is a schematic illustration of exemplary treatment area color markings applied by a color applying element of a treatment unit of an IPL apparatus utilizing a PFN, according to some embodiments of the present invention. The color scheme used in FIG. 9B is defined to clearly present color markings applied by a color applying perimeter edge such as the color applying perimeter edge 912. The colors in FIG. 9B may not be the actual colors applied by the color applying perimeter edge 912. An exemplary color marking 922A (marked in blue) may be applied by the color applying perimeter edge 912 to mark a treatment area 924A (marked in light blue). Similarly, a color marking 922B (marked in red) may be applied by the color applying perimeter edge 912 to mark a treatment area 924B (marked in green). The color markings 922A and 922B may be applied by the color applying perimeter edge 912 when a treatment face such as the treatment face 142 is applied to the respective treatment area 924A and/or 924B.

The color markings 922A and/or 922B may be visible to a user such as the user 160 when illuminated with the appropriate light emitted by the light source(s) 906, for example, a UV light emitted by the UV lamp and/or the UV LED.

The color applying perimeter edge 912 may further apply one or more guide markings, for example, guide markings 926A and 926B when the treatment face 142 is applied to the treatment areas 924A and 924B respectively. The guide markings may allow a user such as the user 160 to align the treatment face 142 over the treatment area treated during a current cycle of the IPL session, for example, the treatment area 924A and/or 924B.

The color markings such as the color markings 922A, 922B, 926A and/or 926B may allow the user 160 using an IPL apparatus such as IPL apparatus 100 to easily and efficiently identify the treatment areas, for example, the treatment areas 924A and 924B which were treated during previous cycles of the IPL session and accurately place the treatment face 142 over the treatment area treated during the current cycle. This may significantly reduce the number of IPL session cycles and hence reduce the IPL session time since by accurately placing the treatment face 142 during each IPL cycle such that the overall area treated during the IPL session is efficiently covered.

The color applying perimeter edge 912 may be adapted to apply the color markings 922A and 922B such that when the treatment face is applied to a certain treatment area, for example, the treatment area 924B, the treatment area 924B at least partially overlaps with at least one other treatment area, for example, the treatment area 924A. This may verify that no area of the overall area treated during the IPL session is left uncovered and hence untreated.

Reference is also made to FIG. 9C, which is a picture of exemplary treatment area color markings applied by a color applying element of a treatment unit of an IPL apparatus utilizing a PFN, according to some embodiments of the present invention. An exemplary color marking 922C may be applied by the color applying perimeter edge 912 to mark a treatment area 924C. The color markings 922C may be applied by the color applying perimeter edge 912 when a treatment face such as the treatment face 142 is applied to the respective treatment area 924C. The color markings 922C may be visible to the user 160 when illuminated with the appropriate light emitted by the light source(s) 906, for example, the UV light emitted by the UV lamp and/or the UV LED.

Reference is made once again to FIG. 9A.

The treatment unit 104A may further comprises a user interface such as the user interface 136 which may include one or more status indication lights 908 which may be used to provide status indications and/or status information to the user 160. In particular, the status indication lights 908 may be located around the perimeter of the treatment face 142 such that the user 160 concentrating on the treatment area may have clear and direct visibility of the status indication lights 908. The user may thus avoid the need to shift his gaze from the treatment area to another location to check the status indication lights 908. The status indication lights 908 may emit light in one or more colors, for example, red, green, yellow, blue and/or the like.

The status indication(s) provided by the status indication light(s) 908 may include, for example, an ON/OFF indication, an operational status indication, a malfunction (failure)

indication and/or the like. For example, the status indication lights 908 may include a ready indication light which may indicate that the PFN 116 is charged and ready to discharge the regulated energized pulse to the lamp(s) 140. Once the ready indication light is activated (e.g. ON, flashing, etc.), after placing the treatment face 142 over the treatment area, the user 160 may initiate a trigger event to instruct release of the regulated energized pulse to cause the lamp(s) 140 to emit the light pulses. In another example, the status indication lights 908 may include a lamp cooling indication light which may indicate status of a cooling progress of the lamp(s) 140. In another example, the status indication lights 908 may include a failure indication light which may indicate of one or more failures in the treatment unit 104A and/or in the base unit 102, for example, failure to charge the capacitor units 210, a failure of a ventilation fan of the treatment unit 104A to cycle air over the lamp(s) 140 for cooling them and/or the like. In another example, the status indication lights 908 may include a maintenance indication light which may indicate of a required maintenance operation, for example, battery replacement and/or the like.

Optionally, one or more of the status indication lights 908 may be operated by a frontend controller such as the front-end control unit 134 in multiple operation modes to provide multiple status indications. The operation modes may include for example, continuous ON or OFF state, flashing at one or more frequencies, emission of different light colors and/or any combination thereof. For example, one or more certain status indication lights 908 may be operated to a steady ON state to indicate one or more of the failure conditions. The certain status indication light(s) 908 may be further operated to flash in a first frequency to indicate that the PFN 116 is charged and ready to discharge the regulated energized pulse. The certain status indication light(s) 908 may also be operated to flash in a second frequency to indicate that the lamp(s) 140 are currently in the cooling down process. In another example, one or more certain status indication lights 908 may be operated to emit a red color in a steady ON state to indicate one or more of the failure conditions. The certain status indication light(s) 908 may be further operated to flash in a first light color (e.g. green) to indicate that the PFN 116 is charged and ready to discharge the regulated energized pulse. The certain status indication light(s) 908 may also be operated to flash in a second light color (e.g. red) to indicate that the lamp(s) 140 are currently in the cooling down process.

Optionally, at least some of the various light sources such as the perimeter illumination light sources 914, the light sources 906 and/or the status indication light 908 are integrated together to construct a unified perimeter lighting source combining at least part of the various light sources. This may simplify the design, construction, production and/or use of the various light sources. This may further simplify control of the front-end control unit 134 to operate the various light sources as well as simplify and potentially reduce cost of the cabling and/or of the provisions required for installing and connecting the various light sources.

The treatment unit 104A may further include one or more assemblies such as the proximity assembly 138 which may be designed, constructed and/or located near the treatment face 142 to monitor proximity to the treatment area. Additionally and/or alternatively the treatment unit 104A may include one or more imaging sensors such as the imaging sensor 144. The imaging sensor(s) 144 may be designed, constructed and/or located near the treatment face 142 similarly to the proximity assembly(s) 138. Optionally, the proximity assembly(s) 138 and the imaging sensor(s) 144 are integrated together and/or are coupled and placed in the same location(s). Optionally, one or more of the proximity assembly 138 is integrated with one or more of the light sources 906 and/or the status indication lights 908 to form an esthetic unified perimeter lighting source.

Figure 10A:
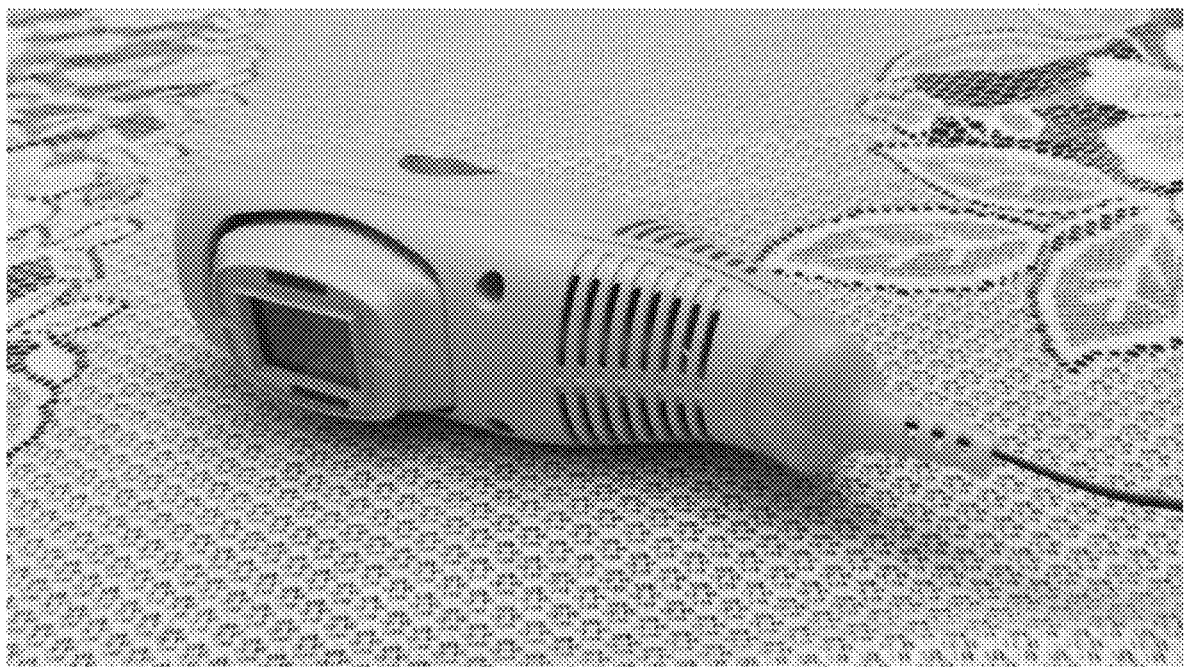
Figure 10B:
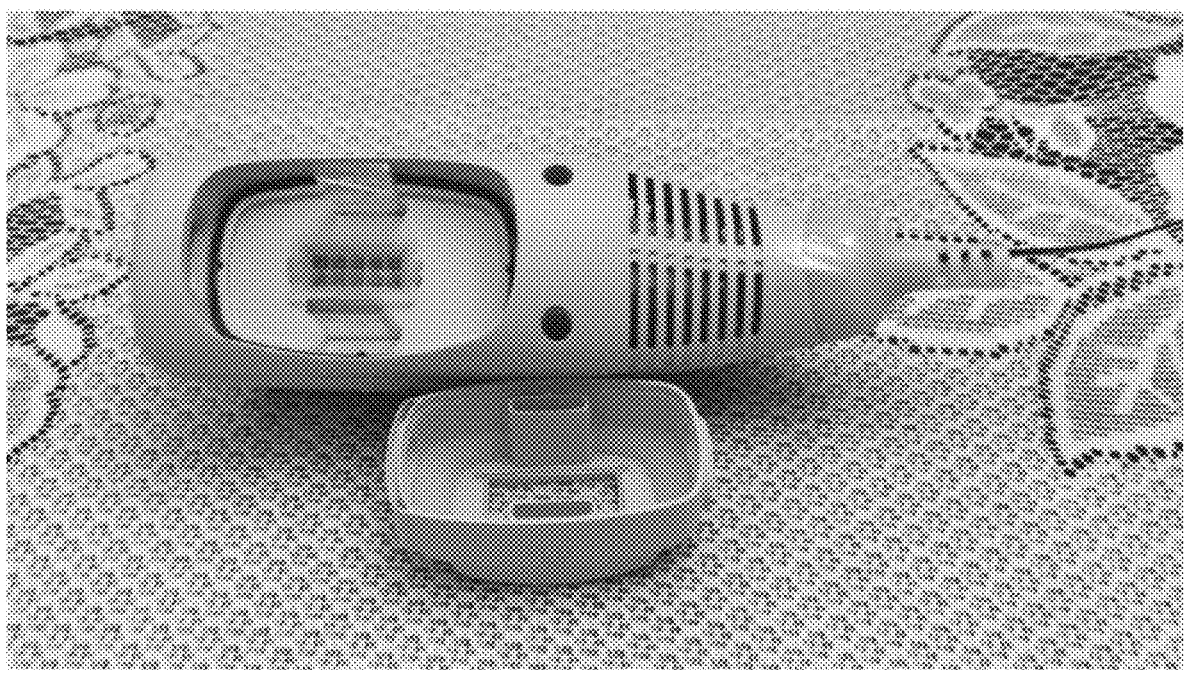
Figure 10C:
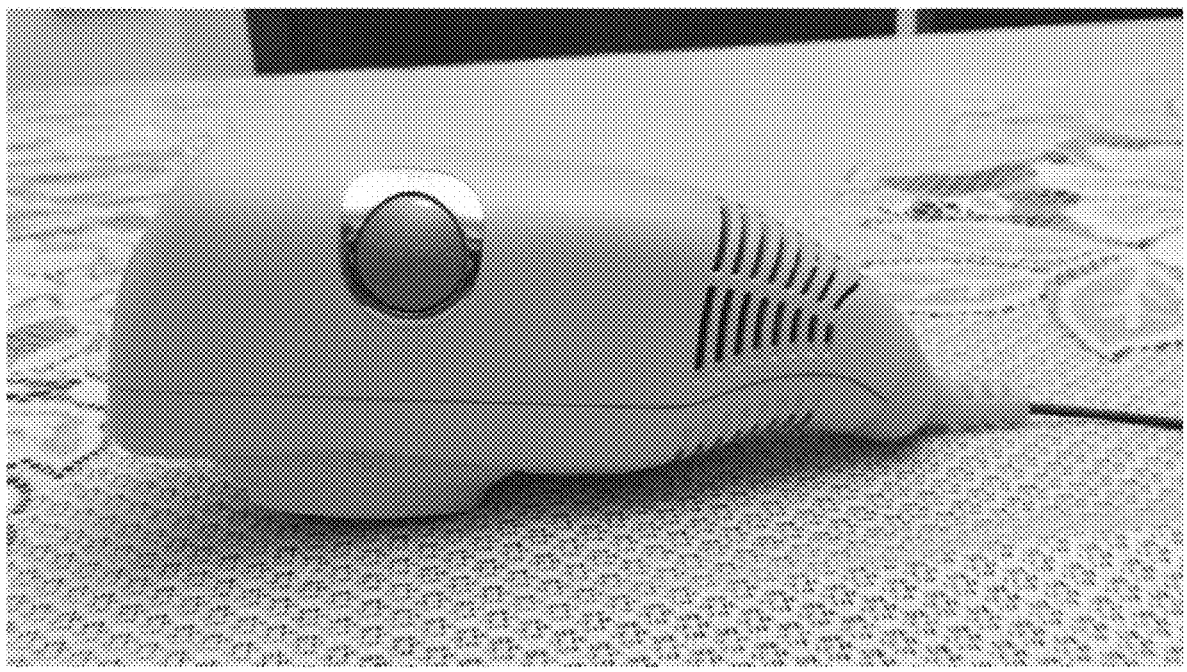
Figure 10D:
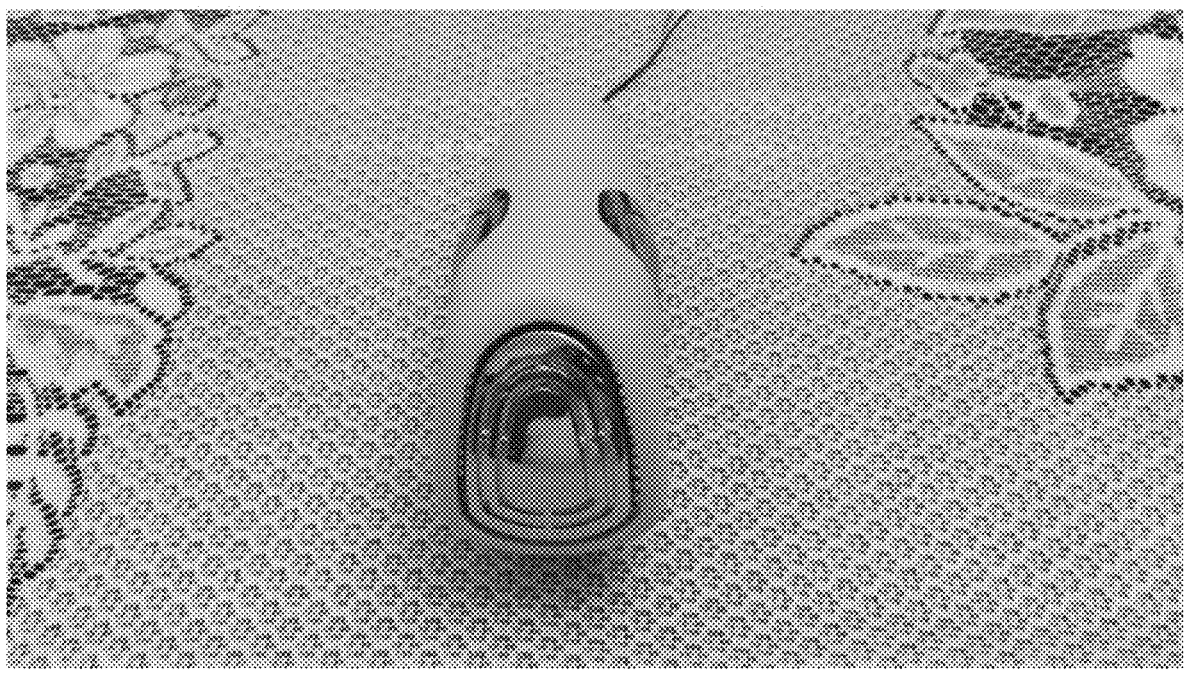

Reference is now made to FIG. 10A, FIG. 10B, FIG. 10C and FIG. 10D, which are captures of a treatment unit of an exemplary IPL apparatus utilizing a PFN, according to some embodiments of the present invention. FIG. 10A, FIG. 10B, FIG. 10C and FIG. 10D present different views of an exemplary treatment unit such as the treatment unit 104A. As shown in FIG. 10A, the treatment unit 104A may be ergonomically shaped for easy and comfortable grip for a user such as the user 160 holding the treatment unit 104A and maneuvering it to the treatment areas on the patient's body. As shown in FIG. 10B, the treatment unit 104A may include a lamp compartment such as the lamp compartment 910 adapted to receive and accommodate one or more lamps such as the lamp 140. The lamp compartment 910 may include a detachable cover which may be removed to remove and/or install the lamp(s) 140 in their designated location(s) in the lamp compartment 910. As shown in FIG. 10C, the treatment unit 104A may include a user interface such as the user interface 136, specifically a trigger button for triggering release of the regulated energized pulse from a PFN such as the PFN 116 to the lamp(s) 140. As shown in FIG. 10D, the treatment unit 104A may include two such trigger buttons adapted for right handed users such as the user 160 and/or for left handed users such as the user 160.

Reference is now made to FIG. 11A, which is a schematic illustration of an exemplary test area of an IPL apparatus utilizing a PFN, according to some embodiments of the present invention. A base unit such as the base unit 102 may optionally include a test area such as the test area 120 for testing a treatment unit such as the treatment unit 104A, in particular for testing one or more lamps such as the lamp 140. The test area 120 may be shaped, located and/or adapted to receive and accommodate the treatment unit 104A, in particular, the test area 120 may be shaped to receive and accommodate a treatment face such as the treatment face 142. One or more light sensors such as the light sensor 122 may be deployed in the test area 120 to capture light emitted by one or more lamps such as the lamp 140 while the treatment face 142 is placed in the test area 120. For example, two light sensors 122 may be placed in the test area 120 such that they are facing the two ends of the lamp(s) 140 when the treatment unit 104A is placed in the test area 120 for testing. In another example, three light sensors 122 may be placed in the test area 120 such that two of the sensors 122 face the two ends of the cylindrically shaped lamp(s) 140 and the $3^{rd}$ light sensor 122 facing a central area of the cylindrically shaped lamp(s) 140 when the treatment unit 104A is placed in the test area 120 for testing.

A main controller such as the control unit 114 may operate a PFN such as the PFN 116 to generate a test regulated energized pulse which may be specifically configured with a multi-level voltage waveform pattern defined for testing one or more emission attributes of the lamp(s) 140. The control unit 114 may collect, obtain and/or receive sensory data from the light sensor(s) 122 and analyze the sensory data to identify values of the emission attributes of one or more of the lamp 140, for example, the level, the intensity, the distribution, the spectrum and/or the like. The control unit 114 may analyze the sensory data according to one or more predefined values indicating the operational status of the lamp(s) 140. For example, a certain intensity threshold may be predefined for a certain lamp 140. In case the measured intensity of the lamp 140 is below the predefined intensity threshold, the control unit 114 may determine the lamp 140 is failed. Based on the identified light emission attribute(s), the control unit 114 may evaluate the operational status of the lamp(s) 140 and determine whether the lamp(s) 140 is operating properly or not. Based on the analysis and determination, the control unit 114 may further inform a user such as the user 160 that one or more of the lamps 140 needs to be replaced. In another example, the control unit 114 may determine the operational status of the lamp(s) 140 by comparing the sensory data be comparing between the values of the emission attribute(s) received form one or more of the light sensors 122. Typically, the lamp(s) 140 may exhibit reduced light emission attributes at the ends of the lamp 140 since these are the locations of electrical contacts feeding the lamp(s) 140. The control unit 114 may therefore compare the emission attributes as recorded by the light sensor 122 located at the center of the lamp(s) 140 to the emission attributes as recorded by one or more of the light sensors 122 located at ends of the lamp(s) 140. It is assumed that the emission attributes captured at the center of the lamp(s) 140 may be indicative of good operational status of the lamp(s) 140. Therefore, based on the comparison the main controller 114 may identify a deviation of the emission attribute(s) captured at the end(s) of the lamp(s) 140.

Reference is also made to FIG. 11B, which is an image capture of a used and/or damaged lamp of an IPL apparatus. FIG. 11B presents a used and/or damaged lamp 140C such as the lamp 140 used for IPL treatments. The damaged lamp 140C has a blackened area 1102 which may affect the emission distribution of the damaged lamp 140C and hence may significantly reduce the effectivity of the IPL treatment. The sensor(s) 122 may be deployed, placed and/or positioned in and/or around the test area 120 to capture light emitted from the lamp(s) 140 over a plurality of locations (spots) of the treatment face 142. The control unit 114 analyzing the sensory data obtained from sensor(s) 122 may thus evaluate the emission characteristic(s) of the light pulses across multiple locations of the treatment face 142. The control unit 114 may therefore be able to detect one or more faulty locations of the lamp(s) 140C, for example, the blackened area 1102 as well as other emission degradation effects.

In some embodiments of the present invention, there is a provided a multi treatment units IPL system comprising an extended base unit that may support multiple treatment units such as the treatment unit 104.

Reference is now made to FIG. 12, which is a schematic illustration of an exemplary IPL apparatus utilizing a PFN and comprising a plurality of treatment units captures of a treatment unit, according to some embodiments of the present invention. A multi treatment units system IPL 1200 may operate as master slave system in which an extended base unit 102A such as the base unit 102 serves as a master to support multiple slave treatment units 104, for example, a treatment unit 104A, a treatment unit 104B to a treatment unit 104N. Each of the treatment units 104 may connect to the extended base unit 102A through a dedicated cable comprising a primary wired interface such as the primary wired interface 150 and optionally an auxiliary wired interface such as the auxiliary wired interface 152. Each of the treatment units 104 may include a wireless communication interface such as the wireless communication interface 132. Using the wireless communication interface 132, a front-end controller such as the front-end controller 134 of one or more of the treatment units 104A through 104N may communicate with a control unit such as the control unit 114 of the extended base unit 102A. One or more of the front-end controllers 134 may communicate with the control unit 114 through a dedicated wireless communication channel. Additionally and/or alternatively, one or more of the front-end controllers 134 may share one or more common wireless communication channels for communicating with the control unit 114. In such implementation(s), each of the treatment units 104 sharing a common wireless communication channel may be assigned a unique identifier (ID) to uniquely identify each treatment unit 104 while communicating with the extended base unit 102A. Each of the treatment units 104A through 104N may be operated by one or more users such as the user 160 where typically each of the treatment units 104A through 104N is operated by a respective user 160A through 160N.

Utilizing a dedicated primary wired interface 150 for each of the treatment units 104 may allow the user(s) 160A through 160N to operate their respective treatment units 104 independently of the other treatment units 104 thus supporting an independent operational environment for each of the treatment units 104. Such a multi treatment units IPL system 1200 may typically be used by professional IPL caregivers to treat simultaneously a plurality of patients and/or treat simultaneously multiple treatment areas of one or more patients.

Reference is now made to FIG. 13, which is a flow chart of an exemplary process executed by an IPL apparatus utilizing a PFN for an IPL treatment, according to some embodiments of the present invention. An exemplary process 1300 may be may be executed by an IPL apparatus such as the IPL apparatus 100, specifically by a control unit such as the control unit 114 of a base unit such as the base unit 102. The control unit 114 may execute the process 100 to generate the regulated energized pulse(s) for feeding one or more IPL lamps such as the lamp 140 which in response may emit sequences of light pulses thus inducing heat over a treatment area of a patient.

As shown at 1302, the control unit 114 may operate a PFN such as the PFN 116 to charge one or more capacitor units such as the capacitor units 210. The control unit 114 may operate the PFN 116 according to one or more parameters of the multi-level voltage waveform of the regulated energized pulse which may be set according to the type of the current IPL treatment and/or according to one or more characteristics of the patient undergoing the IPL treatment. The control unit 114 may obtain the parameters of the multi-level voltage waveform from a user interface such as the user interface 118 operated by a user such as the user 160. Optionally, the user 160 interacts with a user interface such as the user interface 136 of a treatment unit such as the treatment unit 104. In such case the control unit 114 may communicate with a front-end control unit such as the front-end control unit 134 of a treatment unit such as the treatment unit 104 to receive the parameters of the multi-level voltage waveform as instructed by the user 160. The control unit 114 may further operate a power supply such as the power supply 110 of the base unit 102 to adjust the input feed to the capacitor units 210 according to the output voltage level(s) of the desired multi-level voltage waveform.

As shown at 1304, the control unit 114 may generate a ready indication, for example, the ready indication light, the ready sound indication and/or the like to indicate to the user 160 that the PFN 116 is ready to discharge the regulated energized pulse having the desired multi-level voltage waveform. The control unit 114 may generate the ready indication through the user interface 118, for example, activate a ready indication light. Additionally and/or alternatively, the control unit 114 may transmit a ready message and/or signal to the frontend controller which may operate the user interface 136 to indicate the ready state of the PFN 116 to the user 160.

As shown at 1306, which is an optional step, the control unit 114 may initiate a test operation for testing the treatment unit 104, specifically for testing one or more of the lamps 140. While the treatment unit 104 is placed in the designated location of a test area such as the test area 120, the control unit 114 may operate the PFN 116 to discharge the regulated energized pulse. The control unit 114 may obtain sensory data from one or more light sensors such as the light sensors 122 and analyze the sensory data to identify values of one or more of the light emission attributes of the lamp(s) 140, for example, the level, the intensity, the distribution, the spectrum and/or the like. Based on the identified light emission attribute(s), the control unit 114 may evaluate the operational status of the lamp(s) 140 and determine whether the lamp(s) 140 is operating properly or not.

As shown at 1308, the control unit 114 waits for a trigger event initiated by the user 160 to operate the lamp(s) 140 to emit the light pulses in order to induce heat to the treatment area. The control unit 114 may typically receive a trigger message from the front-end control unit 134 communicating with the control unit 114 over one or more of the wireless communication channels. The front-end control unit 134 may detect the trigger event, for example, as a press on the trigger button which may be provided by the user interface 136.

As shown at 1310, the control unit 114 may operate the PFN 116, specifically modules such as the modules 202 to generate the regulated energized pulse having the desired multi-level voltage waveform and drive the regulated energized pulse to the lamp(s) 140 through a primary wired interface such as the primary wired interface 150. For example, the control unit 114 may use one or more PWM elements to control the state (open/close) of one or more switches such as the switch 212. The control unit 114 may also operate the PWM elements to control one or more operational parameters of one or more electrical regulators such as the electrical regulator 214, for example, duty cycle, OFF time period, ON time period, switching frequency and/or the like.

The process 1300 may be repeated for a plurality of IPL session cycles as operated by the user 160. Each cycle of the IPL session may start as step 1302, however the testing step 1304 may be conducted according to instructions received from the user 160, for example, test once after power-up of the IPL apparatus 100, test periodically during the IPL session, test at completion of the IPL treatment and/or the like. The user 160 may select the operation mode using, for example, the test mode button available by the user interface 118 and/or the user interface 136.

It is expected that during the life of a patent maturing from this application many relevant methodologies, materials and/or substances will be developed and the scope of the term IPL lamp is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. An intense pulse light (IPL) apparatus utilizing a pulse forming network (PFN) for generating a plurality of light pulse sequences, comprising:
   a treatment unit comprising at least one lamp adapted to emit a plurality of light pulses towards a treatment face of the IPL apparatus;
   a PFN; and
   a control unit adapted to operate the PFN to generate a regulated energized pulse driven to the at least one lamp, the regulated energized pulse having a desired multi-level voltage waveform comprising a plurality of gradually decreasing high voltage level segments having a maximum voltage level and a plurality of low voltage level segments having a minimum voltage level which is in a range of 30-50 percent of the maximum voltage level such that a voltage level of the multi-level voltage waveform never drops below 30 percent of the maximum voltage level, wherein the plurality of gradually decreasing high voltage level segments and the plurality of low voltage level segments are alternating with one another and are immediately succeeding each other, wherein the plurality of gradually decreasing high voltage level segments having collectively a voltage level which gradual decrease thereof is continuous; wherein rapidly varying heat is induced by a sequence of the plurality of light pulses emitted by the at least one lamp according to the multi-level voltage waveform.

2. The IPL apparatus of claim 1, wherein the control unit is adapted to operate the PFN to generate the multi-level voltage waveform with a first lamp pre-heating pulse comprising a high voltage level segment having a maximum voltage level which is in a range of 40-75 percent of the maximum voltage level.

3. The IPL apparatus of claim 1, wherein the PFN comprising a plurality of capacitor units adapted to store a plurality of charges in a plurality of working voltages, the control unit is adapted to operate a plurality of switches in a sequenced order, each of the plurality of switches is adapted to couple a respective one of the plurality of capacitor units to at least one electrical regulator to form the regulated energized pulse.

4. The IPL apparatus of claim 1, wherein the at least one lamp is a Xenon pulse lamp.

5. The IPL apparatus of claim 1, further comprising an asymmetrically shaped reflector disposed around a plurality of lamps such as the at least one lamp having a cylindrical shape, the asymmetrically shaped reflector is disposed around a longitudinal axis of the plurality of lamps to improve an even illumination distribution of the plurality of light pulses over the treatment face, the reflector is asymmetrically disposed around the longitudinal axis of each of the plurality of lamps such that:
  a low reflection surface of the reflector extending to a height of each lamp is disposed along a side of the longitudinal axis of each lamp facing another lamp of the plurality of lamps, and
  a high reflection surface of the reflector extending above the height of each lamp is disposed along a side of the longitudinal axis of each lamp facing away from any other one of the plurality of lamps.

6. The IPL apparatus of claim 1, wherein the IPL apparatus is constructed of a treatment unit and a base unit, the treatment unit comprises the treatment face, the at least one lamp and a front-end controller, the base unit comprises the PFN and the control unit,
  wherein the base unit drives the regulated energized pulse to the treatment unit through a primary wired interface electrically coupling the PFN to the at least one lamp, and
  the front-end controller communicates with the control unit through at least one wireless communication channel.

7. The IPL apparatus of claim 6, wherein the treatment unit further comprising a power circuit adapted to convert power from the regulated energized pulse for providing power to the treatment unit.

8. The IPL apparatus of claim 6, further comprising the base unit provides power to the treatment unit through an auxiliary wired interface electrically coupling a power source of the base unit to a power circuit of the treatment unit.

9. The IPL apparatus of claim 6, further comprising an extended base unit adapted to drive a respective one of a plurality of regulated energized pulses through a respective one of a plurality of primary wired interfaces to each of a plurality of treatment units such as the treatment unit, wherein the front-end controller of each of the plurality of treatment units communicates with the control unit of the extended base unit through at least one wireless communication channel.

10. The IPL apparatus of claim 1, further comprising the treatment face is at least partially enclosed by a sharpened perimeter edge raised above the treatment face.

11. The IPL apparatus of claim 1, further comprising the treatment face is at least partially enclosed by a color applying perimeter edge raised above the treatment face.

12. The IPL apparatus of claim 11, further comprising at least one light source for illuminating a colored pattern applied to a treatment area by the color applying perimeter edge.

13. The IPL apparatus of claim 1, wherein the control unit is further adapted to verify proper attachment of the treatment face to a treatment area by determining a proximity of the treatment face to the treatment area based on analysis of sensory data obtained from a pair of photodiodes each deployed and adapted to capture a reflection of light emitted by at least one respective light source deployed near the treatment face.

14. The IPL apparatus of claim 13, wherein the control unit is further adapted to adjust the multi-level voltage waveform according to a skin color identified by analyzing sensory data obtained from at least one of the photodiodes.

15. The IPL apparatus of claim 1, wherein the control unit is further adapted to adjust the multi-level voltage waveform according to at least one treatment area characteristic which is a member of a group consisting of: a skin color, a hair color and a hair type, the at least one treatment area characteristic is identified by analyzing at least one image obtained from at least one imaging sensor deployed to depict a treatment area.

16. The IPL apparatus of claim 1, wherein the control unit is adapted to evaluate at least one light emission attribute of the at least one lamp by analyzing sensory data received from a plurality of light sensors exposed to the plurality of light pulses emitted by the at least one lamp.

17. The IPL apparatus of claim 16, wherein the plurality of light sensors are deployed along a longitudinal axis of the at least one lamp to capture the plurality of light pulses in a plurality of locations along the longitudinal axis, the control unit is adapted to analyze the sensory data to identify the at least one light emission attribute for the plurality of locations along the longitudinal axis.

18. A method of using an intense pulse light (IPL) apparatus utilizing a pulse forming network (PFN), comprising:
  operating, at a base unit of an IPL apparatus, a PFN to drive a regulated energized pulse having a desired multi-level voltage waveform comprising a plurality of gradually decreasing high voltage level segments having a maximum voltage level and a plurality of low voltage level segments having a minimum voltage level which is in a range of 30-50 percent of the maximum voltage level such that a voltage level of the multi-level voltage waveform never drops below 30 percent of the maximum voltage level, wherein the plurality of gradually decreasing high voltage level segments and the plurality of low voltage level segments are alternating with one another and are immediately succeeding each other, wherein the plurality of gradually decreasing high voltage level segments having collectively a voltage level which gradual decrease thereof is continuous;

generating a ready indication which indicates the PFN is ready to discharge the regulated energized pulse to at least one lamp adapted to emit a plurality of light pulses towards a treatment face of a treatment unit of the IPL apparatus:

operating, in response to a trigger event, the PFN to discharge the regulated energized pulse, the trigger event is initiated by a user of the IPL apparatus after placing the treatment face on a treatment area;

wherein rapidly varying heat is induced on the treatment area by a sequence of the plurality of light pulses emitted by the at least one lamp according to the multi-level voltage waveform.

19. The method of claim 18, further comprising testing the at least one lamp by operating the PFN to drive a test regulated energized pulse to the at least one lamp while the treatment unit is located in a test area of the IPL apparatus shaped to receive and accommodate the treatment unit, and evaluating at least one light emission attribute of the at least one lamp by analyzing sensory data received from a plurality of sensors deployed in the test area along a longitudinal axis of the at least one lamp and exposed to the plurality of light pulses emitted by the at least one lamp according to the multi-level voltage waveform of the test regulated energized pulse.

20. The IPL apparatus of claim 1, wherein at least a subset of the plurality of low voltage level segments have a same voltage level.

* * * * *